US012637448B2

(12) United States Patent
Wu et al.

(10) Patent No.: US 12,637,448 B2
(45) Date of Patent: May 26, 2026

(54) TRICYCLIC COMPOUNDS AND USE THEREOF

(71) Applicants: HELIOEAST PHARMACEUTICAL CO., LTD, Nanchang (CN); HELIOEAST SCIENCE & TECHNOLOGY CO., LTD., Nanchang (CN)

(72) Inventors: Lingyun Wu, Shanghai (CN); Peng Yang, Shanghai (CN); Lele Zhao, Shanghai (CN); Jian Li, Shanghai (CN); Shuhui Chen, Shanghai (CN)

(73) Assignees: HELIOEAST PHARMACEUTICAL CO., LTD, Nanchang (CN); HELIOEAST SCIENCE & TECHNOLOGY CO., LTD., Nanchang (CN)

( * ) Notice: Subject to any disclaimer, the term of this patent is extended or adjusted under 35 U.S.C. 154(b) by 837 days.

(21) Appl. No.: 17/905,534

(22) PCT Filed: Mar. 2, 2021

(86) PCT No.: PCT/CN2021/078744
§ 371 (c)(1),
(2) Date: Sep. 2, 2022

(87) PCT Pub. No.: WO2021/175225
PCT Pub. Date: Sep. 10, 2021

(65) Prior Publication Data

US 2023/0124301 A1 Apr. 20, 2023

(30) Foreign Application Priority Data

Mar. 4, 2020 (CN) ......................... 202010144417.0
May 27, 2020 (CN) ......................... 202010464135.9

(51) Int. Cl.
*C07D 413/14* (2006.01)
*C07D 401/14* (2006.01)
*C07D 417/14* (2006.01)

(52) U.S. Cl.
CPC ......... *C07D 413/14* (2013.01); *C07D 401/14* (2013.01); *C07D 417/14* (2013.01)

(58) Field of Classification Search
CPC .. C07D 413/14; C07D 401/14; C07D 417/14; A61P 37/00
See application file for complete search history.

(56) References Cited

U.S. PATENT DOCUMENTS 10,981,900 B2 * 4/2021 Zhang .................. C07D 409/04
2012/0101083 A1 4/2012 Bailey
2020/0048235 A1 2/2020 Zhang et al.

FOREIGN PATENT DOCUMENTS

CN 102724880 A 10/2012
CN 107857760 A 3/2018
JP 2007515432 A 6/2007
JP 2012530108 A 11/2012
WO 2005058848 A1 6/2005
WO 2010148649 A1 12/2010
WO 2011060389 A1 5/2011
WO 2011060392 A1 5/2011
WO 2018028557 A1 2/2018
WO 2018157813 A1 9/2018

OTHER PUBLICATIONS

Patani, G. A., LaVoie, E. J.; Chemical Reviews, v96, pp. 3147-3176; 1996 (Year: 1996).*
Japanese Notice of Reasons for Refusal issued in Japanese Patent Application No. 2022-552682 dated Oct. 3, 2023, with English language translation, 5 pages.
International Search Report for International Patent Application No. PCT/CN2021/078744 dated Apr. 25, 2021, 7 pages including English translation.
Written Opinion of the International Searching Authority for International Patent Application No. PCT/CN2021/078744 dated Apr. 25, 2021, 6 pages including English translation.
Chinese Office Action issued in Chinese Patent Application No. 202180018848.5 dated Sep. 14, 2024, 11 pages including English translation.
Sarakinos, G., Supplementary European Search Report issued in European Patent Application No. 21765186.8 dated Jun. 30, 2023, 9 pages.
Chinese Search Report issued in Chinese Patent Application No. 202180018848.5 dated Feb. 29, 2024, 4 pages including English translation.

(Continued)

*Primary Examiner* — Jeffrey S Lundgren
*Assistant Examiner* — W. Justin Youngblood
(74) *Attorney, Agent, or Firm* — MH2 Technology Law Group LLP

(57) ABSTRACT

Disclosed in the present invention are a series of tricyclic compounds, and particularly disclosed are a compound shown in formula (I) or a pharmaceutically acceptable salt thereof.

(I)

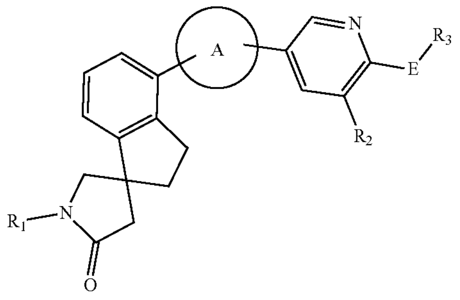

10 Claims, No Drawings

(56) References Cited

OTHER PUBLICATIONS

Chinese First Office Action issued in Chinese Patent Application No. 202180018848.5 mailed Mar. 4, 2024, 9 pages including English translation.

* cited by examiner

TRICYCLIC COMPOUNDS AND USE THEREOF

CROSS-REFERENCE TO RELATED APPLICATIONS

The present application is a U.S. National Stage application of PCT/CN2021/078744 filed 2 Mar. 2021, which claims priority to Chinese Patent Application No. 202010144417.0 filed 4 Mar. 2020 and Chinese Patent Application No. 202010464135.9 filed 27 May 2020, the entire disclosures of which are hereby incorporated by reference in their entireties.

TECHNICAL FIELD

The present disclosure relates to a class of tricyclic compounds, in particular to a compound represented by formula (I) or a pharmaceutically acceptable salt thereof.

BACKGROUND

Sphingosine-1-phosphate (S1P) is a lysophospholipid signaling molecule derived from a cell membrane, which mainly exerts physiological functions by stimulating some members of the G protein-coupled receptor family, mainly sphingosine-1-phosphate receptors (S1PRs) family At present, five different S1PR subtypes have been identified in mammals, including sphingosine-1-phosphate receptor 1 (S1PR1 or EDG1), sphingosine-1-phosphate receptor 2 (S1PR2 or EDGS), sphingosine-1-phosphate receptor 3 (S1PR3 or EDG3), sphingosine-1-phosphate receptor 4 (S1PR4 or EDG6) and sphingosine-1-phosphate receptor 5 (S1PR5 or EDG8). S1PR1-3 are widely expressed in various tissues, S1PR4 is mainly expressed in lymphatic system and blood system, and S1PR5 is mainly expressed in the central nervous system. Lymphocytes sense a S1P concentration gradient through S1PR1, thereby regulating the entry of lymphocytes from secondary lymphoid organs into the lymph and blood circulation. S1PR1 agonists can trigger the endocytosis of S1PR1 on the surface of lymphocytes, make the lymphocytes unable to sense the S1P concentration gradient, prevent the migration of lymphocytes to the lymph and blood circulation, trigger the homing of lymphocytes, reduce the number of lymphocytes in the peripheral circulatory system, and prevent the lymphocytes from reaching the position of inflammatory lesions or grafts, reduces excessive inflammation, and have immunomodulatory effect.

Autoimmune disease refers to a general term for a class of diseases caused by the body's immune response to autoantigen, causing the immune system to mistakenly attack its own tissues. At present, there are more than 80 kinds of autoimmune diseases that are precisely defined, and excessive inflammatory reaction is a common feature. S1PR1 agonists can effectively reduce excessive inflammation, and can be used to treat or prevent autoimmune diseases, including multiple sclerosis, inflammatory bowel disease (divided into Crohn's disease and ulcerative colitis), systemic lupus erythematosus and psoriasis, etc.

At present, the efficacy studies of S1PR1 agonists in vivo are used to treat or prevent autoimmune diseases. Fingolimod, the first-generation non-selective S1PRs agonist of Novartis, was approved by FDA for relapsing multiple sclerosis (RMS) in September 2010. Siponimod, the second-generation selective S1PR1 and S1PR5 agonist of Novartis, was also approved by FDA for relapsing multiple sclerosis (RMS) in March 2019. The discovery and application of novel S1PR agonists holds great promise.

CONTENT OF THE PRESENT INVENTION

The present disclosure provides a compound represented by formula (I) or a pharmaceutically acceptable salt thereof, (I)

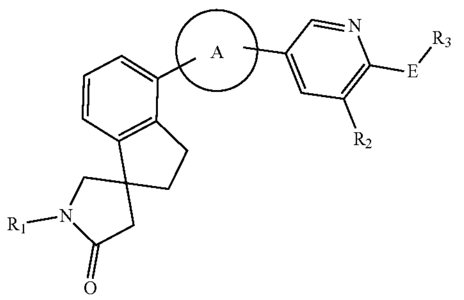

wherein,

E is selected from O;

ring A is selected from oxazolyl, 1,2,4-oxadiazolyl, thiazolyl, 1,3,4-thiadiazolyl, 1,2,4-thiadiazolyl, pyrimidinyl and pyrazinyl;

$R_1$ is selected from $C_{1-3}$ alkyl and cyclobutyl, and the $C_{1-3}$ alkyl and cyclobutyl are optionally substituted by 1, 2 or 3 $R_a$;

$R_2$ is selected from F, Cl, Br, CN and $CHF_2$;

$R_3$ is selected from $C_{1-6}$ alkyl, and the $C_{1-6}$ alkyl is optionally substituted by 1, 2 or 3 $R_b$;

$R_a$ is independently selected from F, Cl, Br, OH, $NH_2$ and COOH, respectively;

$R_b$ is independently selected from F, Cl and Br, respectively.

In some embodiments of the present disclosure, the ring A is selected from

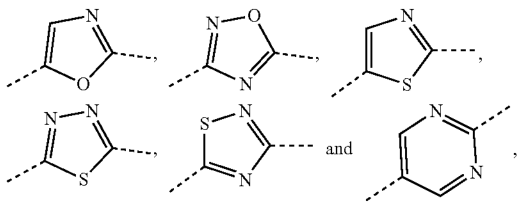

, , , , and , and other variables are defined in the present disclosure.

In some embodiments of the present disclosure, the $R_a$ is independently selected from OH and COOH, respectively, and the other variables are defined in the present disclosure.

In some embodiments of the present disclosure, the $R_1$ is selected from $CH_3$, $CH_2CH_3$, $CH_2CH_2CH_3$ and

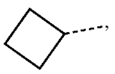

and the $CH_3$, $CH_2CH_3$ and

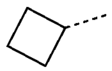

are optionally substituted by 1, 2 or 3 $R_a$, and the other variables are defined in the present disclosure.

In some embodiments of the present disclosure, the $R_1$ is selected from $CH_2CH_2OH$, $CH_2COOH$, $CH_2CH_2COOH$ and

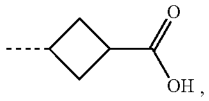

and the other variables are defined in the present disclosure.

In some embodiments of the present disclosure, the $R_2$ is selected from Br and CN, and the other variables are defined in the present disclosure.

In some embodiments of the present disclosure, the $R_3$ is selected from $C_{1-3}$ alkyl, and the $C_{1-3}$ alkyl is optionally substituted by 1, 2 or 3 $R_b$, and the other variables are defined in the present disclosure.

In some embodiments of the present disclosure, the $R_3$ is selected from $CH(CH_3)_2$, and the other variables are defined in the present disclosure.

In some embodiments of the present disclosure, the structural moiety is

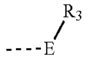

selected from

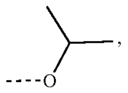

and other variables are defined in the present disclosure.

In some embodiments of the present disclosure, the compound or the pharmaceutically acceptable salt thereof is selected from:

(I-1)

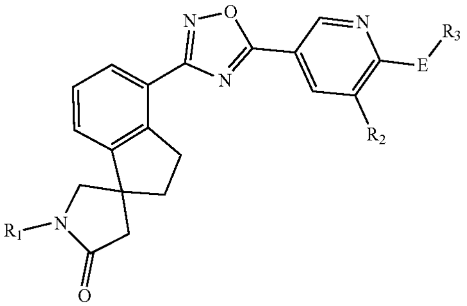

-continued (I-2)

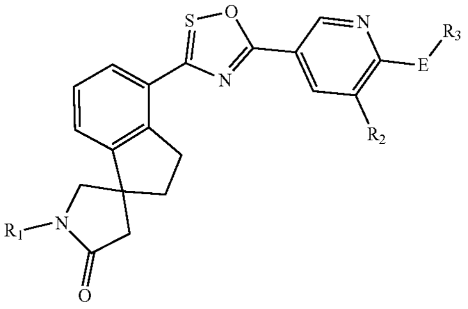

(I-3)

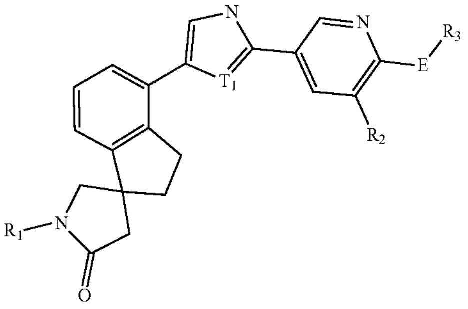

(I-4)

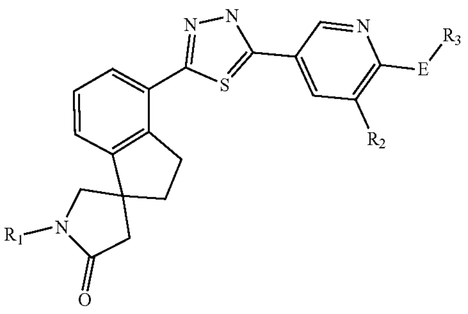

wherein, $R_1$, $R_2$, $R_3$ and E are defined as above;

$T_1$ is selected from O and S.

There are also some embodiments of the present disclosure obtained by an arbitrary combination of the above variables.

The present disclosure also provides a compound represented by the following formula or a pharmaceutically acceptable salt thereof,

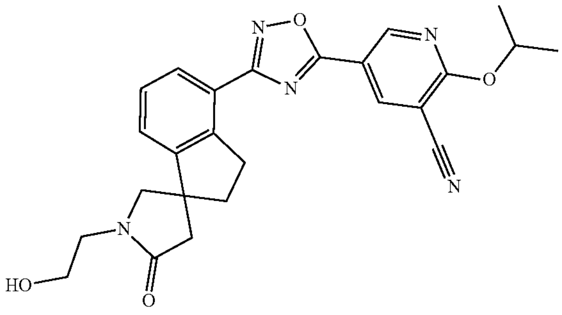

-continued

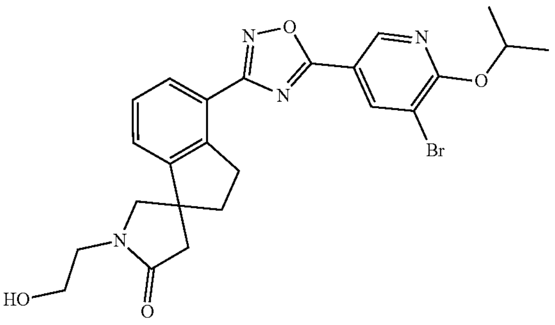

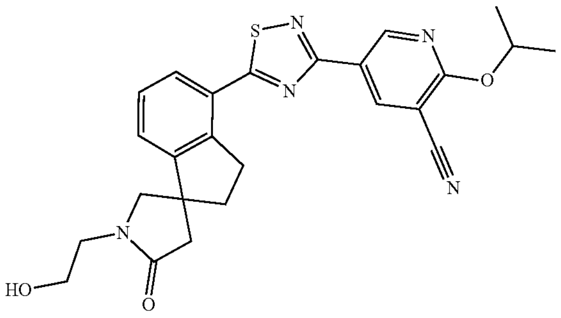

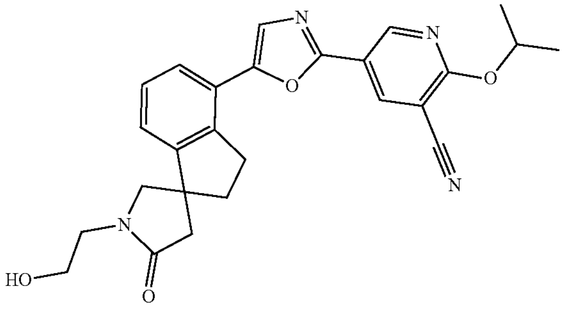

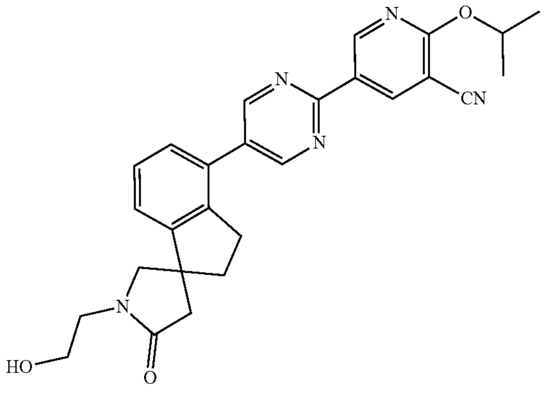

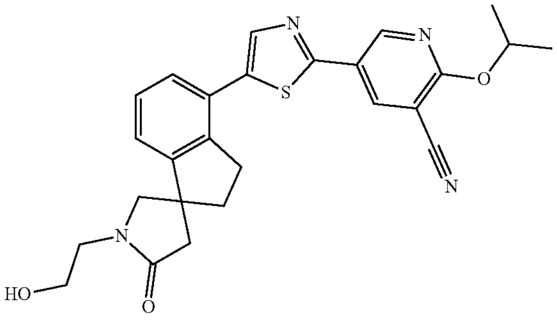

-continued

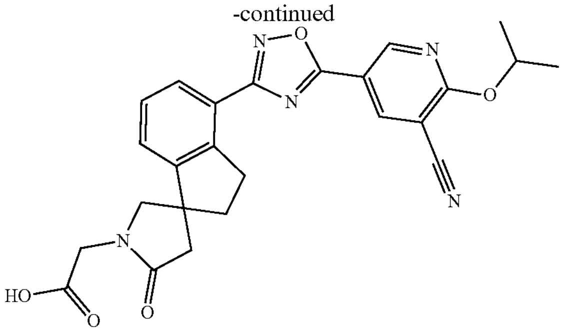

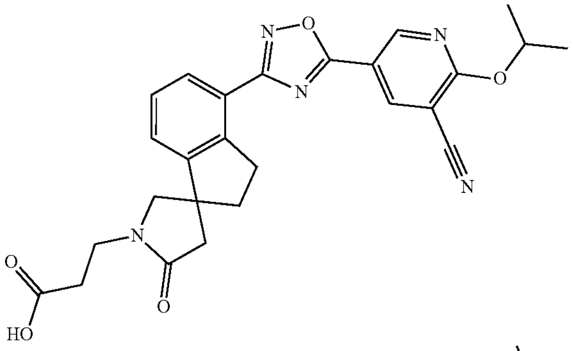

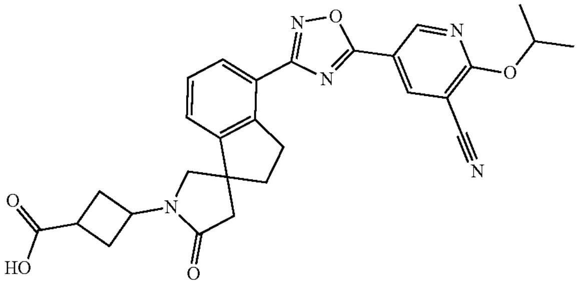

and

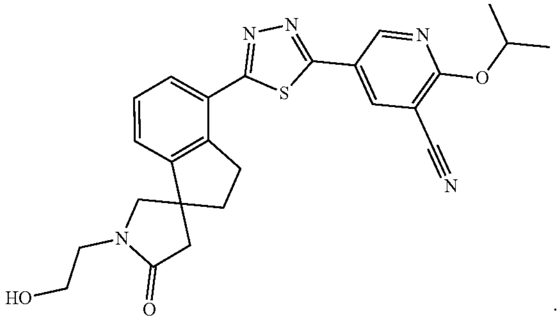

.

The present disclosure also provides use of the above compound or the pharmaceutically acceptable salt thereof in the manufacture of a medicament for treating diseases related to S1PR1.

Technical Effect

The compounds of the present disclosure have significant or even unexpected S1PR1 agonistic activity and good bioavailability.

Related Definitions

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)-and (+)-enantiomers, (R)-and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

The compound of the present disclosure may contain an unnatural proportion of atomic isotope at one or more than one atom(s) that constitute the compound. For example, the compound can be radiolabeled with a radioactive isotope, such as tritium ($^{3}H$), iodine-125 ($^{125}I$) or C-14 ($^{14}C$). For another example, deuterated drugs can be formed by replacing hydrogen with deuterium, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as $-(CRR)_0-$, it means that the linking group is a single bond.

When one of the variables is selected from a single bond, it means that the two groups linked by the single bond are connected directly. For example, when L in A-L-Z represents a single bond, the structure of A-L-Z is actually A-Z.

Unless otherwise specified, when a group has one or more linkable sites, any one or more sites of the group can be linked to other groups through chemical bonds. When the linking site of the chemical bond is not positioned, and there is H atom at the linkable site, then the number of H atom at the site will decrease correspondingly with the number of chemical bond linking thereto so as to meet the corresponding valence. The chemical bond between the site and other groups can be represented by a straight solid bond (), a straight dashed bond () or a wavy line (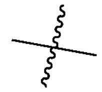).

For example, the straight solid bond in $-OCH_3$ means that it is linked to other groups through the oxygen atom in the group; the straight dashed bonds in

means that it is linked to other groups through the two ends of nitrogen atom in the group; the wave lines in

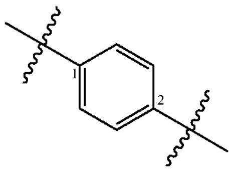 [SMILES: *c1ccc(*)cc1]

means that the phenyl group is linked to other groups through carbon atoms at position 1 and position 2;

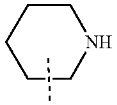

means that it can be linked to other groups through any linkable sites on the piperidinyl by one chemical bond, including at least four types of linkage, including

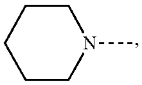,
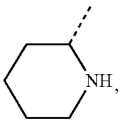,
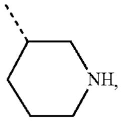,
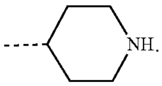.

Even though the H atom is drawn on the —N—,

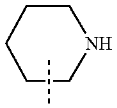

still includes the linkage of

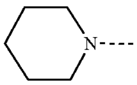, merely when one chemical bond is connected, the H of this site will be reduced by one to the corresponding monovalent piperidinyl.

Unless otherwise specified, the term "$C_{1-6}$ alkyl" refers to a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl and the like; it can be monovalent (such as methyl), divalent (such as methylene) or multivalent (such as methine). Examples of $C_{1-6}$ alkyl include but are not limited to methyl (Me), ethyl (Et), propyl (including n-propyl and isopropyl), butyl (including n-butyl, isobutyl, s-butyl, and t-butyl), pentyl (including n-pentyl, isopentyl and neopentyl), hexyl and the like.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl) and the like.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$ and the like; similarly, n-membered to n+m-membered means that the number of atoms on the ring is from n to n+m, for example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring, and any range from n to n+m is also included, for example, 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring and the like.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/ω scan, and after collecting the relevant data, the crystal structure can be further analyzed by direct method (Shelxs97).

The solvent used in the present disclosure is commercially available.

The compounds of the present disclosure are named according to the conventional naming principles in the art or by ChemDraw® software, and the commercially available compounds use the supplier catalog names.

DETAILED DESCRIPTION OF THE PREFERRED EMBODIMENT

The following embodiments further illustrate the present disclosure, but the present disclosure is not limited thereto. The present disclosure has been described in detail herein, and its specific embodiments have also been disclosed, for one skilled in the art, it is obvious to make various modifications and improvements to the embodiments of the present disclosure without departing from the spirit and scope of the present disclosure.

Embodiment 1
Compound 1
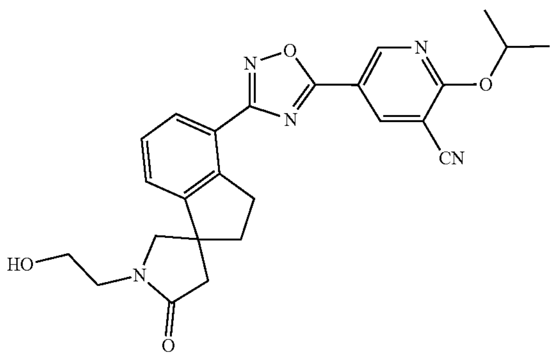
Synthetic Route:
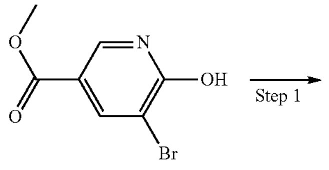
1a
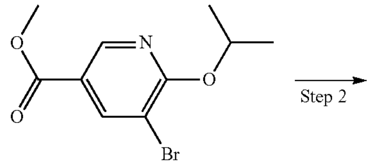
1b
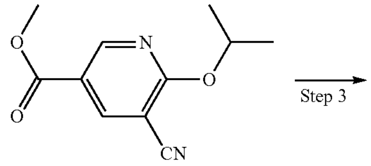
1c
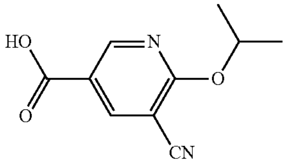
1d
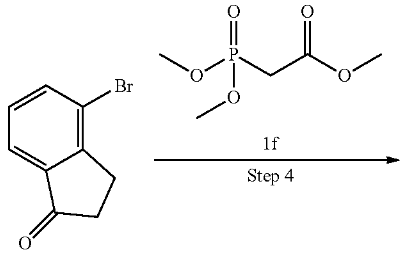
1e
-continued
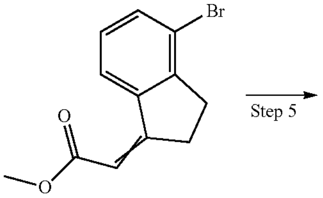
1g
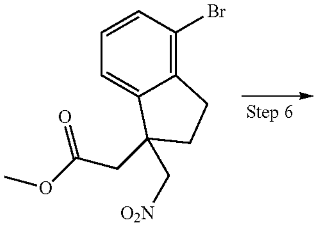
1h
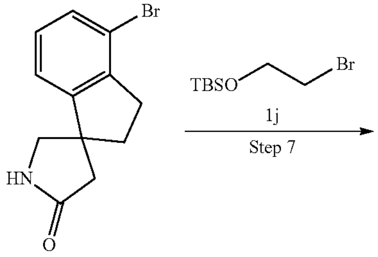
1i
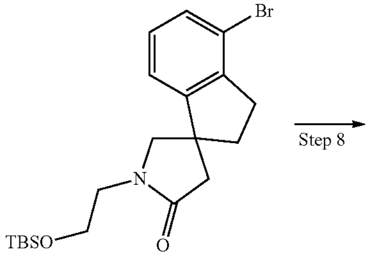
1k
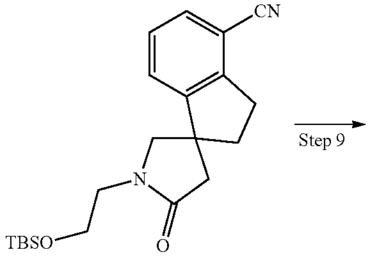
1l -continued

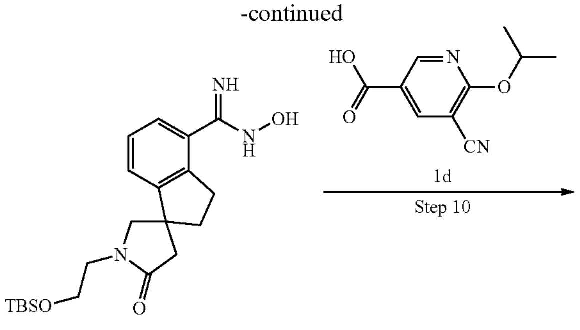

1m

Compound 1

Step 1

Compound 1a (1.00 g, 4.31 mmol) and 2-iodopropane (1.47 g, 8.62 mmol) were dissolved in toluene (8 mL), then silver carbonate (3.57 g, 12.9 mmol) was added thereto, and the reaction solution was stirred at 50° C. for 16 hours. The reaction solution was concentrated under reduced pressure, and the residue was diluted with water (100 mL), extracted with ethyl acetate (100 mL×3). The combined organic phases were washed with saturated brine (100 mL×1), dried with anhydrous sodium sulfate, filtered, and the filtrate was concentrated under reduced pressure to obtain compound 1b.

MS-ESI calculated for $[M+H]^+$ 274 and 276, found 274 and 276.

$^1H$ NMR (400 MHz, $CDCl_3$) δ=8.72 (d, J=2.1 Hz, 1H), 8.38 (d, J=2.1 Hz, 1H), 5.48-5.37 (m, 1H), 3.92 (s, 3H), 1.42 (d, J=6.2 Hz, 6H).

Step 2

Compound 1b (1.00 g, 3.65 mmol) was dissolved in anhydrous N,N-dimethylformamide (15 mL), and then zinc cyanide (857 mg, 7.30 mmol), tris(dibenzylideneacetone) dipalladium (334 mg, 365 μmol) and 2-di-tert-butylphosphino-2',4',6'-triisopropylbiphenyl (348 mg, 730 μmol) were added thereto. The reaction solution was stirred at 90° C. for 12 hours under nitrogen protection. The reaction solution was concentrated, and the residue was diluted with water (50 mL), extracted with ethyl acetate (30 mL×3). The combined organic phases were washed with saturated brine (40 mL×1), dried with anhydrous sodium sulfate, concentrated, and the crude product was purified by silica gel column chromatography (10:1, petroleum ether/ethyl acetate, Rf=0.4) to obtain compound 1c.

MS-ESI calculated for $[M+H-^iPr]^+$ 179, found 179.

Step 3

Compound 1c (100 mg, 454 μmol) was dissolved in tetrahydrofuran (1 mL) and methanol (0.5 mL), and a solution of lithium hydroxide monohydrate (57.2 mg, 1.36 mmol) in water (0.5 mL) was added dropwise to the reaction solution, and the reaction solution was stirred at 25° C. for 1 hour. The reaction solution was concentrated under reduced pressure to remove the organic solvent. The pH of the residue was adjusted to about 6 with 1 N aqueous hydrochloric acid solution, then the mixture was diluted with water (50 mL) and extracted with ethyl acetate (50 mL×3). The combined organic phases were dried with anhydrous sodium sulfate, filtered and concentrated to obtain the crude product. The crude product was purified by thin-layer silica gel chromatography (10:1, dichloromethane/methanol, Rf=0.21) to obtain compound 1d.

$^1H$ NMR (400 MHz, $CDCl_3$) δ=9.18-8.74 (m, 1H), 8.70-8.23 (m, 1H), 5.60-5.38 (m, 1H), 1.43 (d, J=6.1 Hz, 6H).

Step 4

Compound 1f (56.0 g, 308 mmol) was dissolved in N,N-dimethylformamide (200 mL), and potassium tert-butoxide (34.6 g, 308 mmol) was added thereto. The reaction solution was stirred at 25° C. for 2 hours, then compound 1e (50.0 g, 237 mmol) was slowly added thereto, and the reaction solution was stirred at 25° C. for 12 hours. The reaction solution was added with water (800 mL), extracted with ethyl acetate (400 mL×3), and the organic phases were combined. The organic phases were washed with water (500 mL×1) and saturated brine (500 mL×1) respectively. The organic phases were dried with anhydrous sodium sulfate, concentrated, and the crude product was purified by column chromatography (10:1, petroleum ether/ethyl acetate, Rf=0.6, 0.7) to obtain compound 1 g.

MS-ESI calculated for $[M+H]^+$ 267 and 269, found 267 and 269.

$^1H$ NMR (400 MHz, $CDCl_3$) δ=7.57-7.48 (m, 1H), 7.39-7.29 (m, 1H), 7.24-7.10 (m, 1H), 6.55-6.27 (m, 1H), 3.81-3.70 (m, 3H), 3.63-3.37 (m, 2H), 3.33-3.00 (m, 2H).

Step 5

Compound 1g (100 g, 374 mmol) was dissolved in dimethyl sulfoxide (400 mL), and cesium carbonate (97.6 g, 299 mmol) was added thereto, and then nitromethane (68.6 g, 1.12 mol) was slowly added dropwise. The reaction solution was stirred at 70° C. for 16 hours. The mixture was added with water (1600 mL) to quench the reaction, extracted with ethyl acetate (800 mL×3), and the combined organic phases were washed with water (1000 mL×1) and saturated brine (1000 mL×1) respectively, dried with anhydrous sodium sulfate, and concentrated to obtain compound 1h.

$^1H$ NMR (400 MHz, $CDCl_3$) δ=7.41 (dd, J=7.2, 1.6 Hz, 1H), 7.12-7.04 (m, 2H), 4.89 (d, J=11.6 Hz, 1H), 4.81 (d, J=11.6 Hz, 1H), 3.86 (s, 3H), 3.04-2.96 (m, 3H), 2.78 (d, J=16.4 Hz, 1H), 2.44-2.35 (m, 1H), 2.26-2.16 (m, 1H).

Step 6

Compound 1h (100 g, 305 mmol) was dissolved in a mixed solvent of ethanol (300 mL) and water (100 mL), and then ammonium chloride (48.90 g, 914 mmol) and iron powder (51.1 g, 914 mmol) were added thereto. The reaction solution was stirred at 80° C. for 15 hours. The reaction solution was filtered with diatomite, and the filtrate was diluted with water (1000 mL), extracted with ethyl acetate (500 mL×3). The combined organic phases were washed with saturated brine (500 mL×1) respectively, dried with anhydrous sodium sulfate, and concentrated. The crude product was added to a mixed solution of ethyl acetate/n-heptane (1:6, 1180 mL), and the mixture was stirred at 25° C. for 3 days, filtered, and the filter cake was dried under vacuum to obtain compound 1i.

MS-ESI calculated for $[M+H]^+$ 266 and 268, found 266 and 268.

$^1$H NMR (400 MHz, $CDCl_3$) δ=7.52-7.32 (m, 1H), 7.25-7.06 (m, 2H), 7.06-6.87 (m, 1H), 3.63-3.32 (m, 2H), 3.08-2.83 (m, 2H), 2.69-2.41 (m, 2H), 2.36-2.10 (m, 2H).

Step 7

Compound 1i (182 g, 589 mmol) and compound 1j (422 g, 1.77 mol) were dissolved in N,N-dimethylformamide (360 mL), and then cesium carbonate (575 g, 1.77 mol) and sodium iodide (44.1 g, 294 mmol) were added thereto, and then the reaction solution was stirred at 80° C. for 16 hours. The reaction solution was filtered, and the filter cake was washed with ethyl acetate (400 mL×4). The filtrate was diluted with water (4000 mL), then the phases were separated to collect the organic phase, and the aqueous phase was extracted with ethyl acetate (2000 mL×2). The combined organic phases were washed with saturated brine (2000 mL×2), dried with anhydrous sodium sulfate, filtered, and the filtrate was concentrated under reduced pressure to obtain compound 1k.

MS-ESI calculated for $[M+H]^+$ 424 and 426, found 424 and 426.

Step 8

Compound 1k (470 g, 587 mmol) was dissolved in anhydrous N,N-dimethylformamide (1200 mL), and then zinc cyanide (103 g, 880 mmol), tris(dibenzylideneacetone) dipalladium (21.5 mg, 23.5 mmol) and 2-di-tert-butylphosphino-2',4',6'-triisopropylbiphenyl (22.4 mg, 47.0 mmol) were added to the reaction solution in turn. The reaction solution was stirred at 90° C. for 16 hours under nitrogen protection. The reaction solution was concentrated under reduced pressure, and water (6000 mL) was added to the residue, and the mixture was extracted with ethyl acetate (2000 mL×3). The organic phases were combined, washed with saturated brine (2000 mL×1), and dried with anhydrous sodium sulfate, filtered, and concentrated. The crude product was filtered with neutral alumina (800 g), and the filter cake was washed with a mixed solvent of petroleum ether/ethyl acetate/dichloromethane (3/1/1, 15 L). The filtrate was concentrated under reduced pressure, and the crude product was diluted with n-heptane (1.0 L), and the mixture was stirred at 25° C. for 16 hours, and filtered. The filter cake was diluted again with n-heptane (500 mL), and the mixture was stirred at 25° C. for 16 hours, and filtered. The filter cake was washed with n-heptane (150 mL×1), and the filter cake was dried under vacuum to obtain compound 1l.

MS-ESI calculated for $[M+H]^+$ 371, found 371.

Step 9

Compound 1l (120 g, 324 mmol) was dissolved in ethanol (600 mL), and then diisopropylethylamine (83.7 g, 647 mmol) and hydroxylamine hydrochloride (45.0 g, 647 mmol) were added in turn, and the reaction solution was stirred at 40° C. for 16 hours. The mixture was added with water (700 mL) to dilute, extracted with ethyl acetate (400 mL×3), and the combined organic phases were washed with saturated brine (400 mL×2), dried with anhydrous sodium sulfate, filtered, and concentrated under reduced pressure. The residue was added to a mixed solution of n-heptane/isopropanol (5/1, 560 mL), and the mixture was stirred at 15° C. for 65 hours, filtered. The filter cake was washed with a mixed solution of n-heptane/isopropanol (5:1, 100 mL×2), and the filter cake was dried under vacuum to obtain compound 1m.

$^1$H NMR (400 MHz, $CDCl_3$) δ=7.45-7.37 (m, 1H), 7.31-7.25 (m, 2H), 4.84 (s, 2H), 3.81 (t, J=5.3 Hz, 2H), 3.67 (d, J=9.6 Hz, 1H), 3.61 (d, J=9.6 Hz, 1H), 3.48 (t, J=5.3 Hz, 2H), 3.13 (t, J=7.1 Hz, 2H), 2.69 (d, J=16.8 Hz, 1H), 2.59 (d, J=16.8 Hz, 1H), 2.33-2.08 (m, 2H), 0.89 (s, 9H), 0.10-0.04 (m, 6H).

Step 10

Compound 1d (51.1 mg, 248 μmol) was dissolved in N,N-dimethylformamide (2 mL), and then 1-(3-dimethylaminopropyl)-3-ethylcarbodiimide hydrochloride (57.0 mg, 297 μmol) and 1-hydroxybenzotriazole monohydrate (40.2 mg, 297 μmol) were added to the solution. The reaction solution was stirred at 25° C. for 15 minutes. Then compound 1m (100 mg, 248 μmol) was added thereto, and the mixture was stirred at 25° C. for 1 hour and stirred at 80° C. for 16 hours. The reaction solution was diluted with water (50 mL), extracted with ethyl acetate (50 mL×3), and the combined organic phases were dried with anhydrous sodium sulfate, filtered, and the filtrate was concentrated under reduced pressure. The crude product was purified by high performance liquid chromatography {hydrochloric acid condition, column type: Phenomenex Luna C18 150*25 mm*10 μm; mobile phase: [water (0.05% HCl)-acetonitrile]; acetonitrile %: 43%-73%, 10 minutes} to obtain compound 1.

MS-ESI calculated for $[M+H]^+$ 460, found 460.

$^1$H NMR (400 MHz, $CDCl_3$) δ=9.16 (d, J=2.3 Hz, 1H), 8.65 (d, J=2.3 Hz, 1H), 8.11-8.08 (m, 1H), 7.46-7.41 (m, 2H), 5.62-5.51 (m, 1H), 3.89-3.82 (m, 2H), 3.69-3.61 (m, 2H), 3.57-3.47 (m, 2H), 3.43-3.32 (m, 2H), 2.79 (d, J=16.9 Hz, 1H), 2.69 (d, J=16.9 Hz, 1H), 2.41-2.23 (m, 2H), 1.48 (d, J=6.2 Hz, 6H).

Embodiment 3

Compound 3

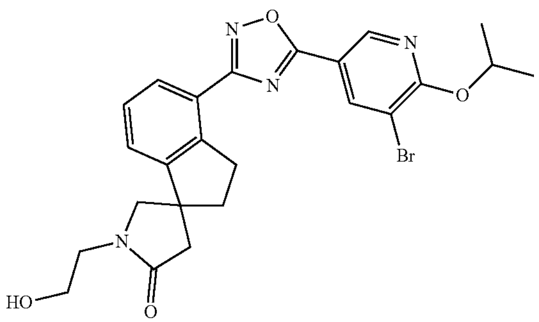

Synthetic Route:

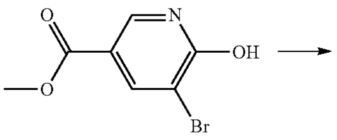

3a

-continued

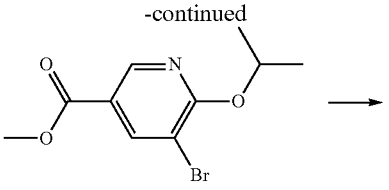

3b

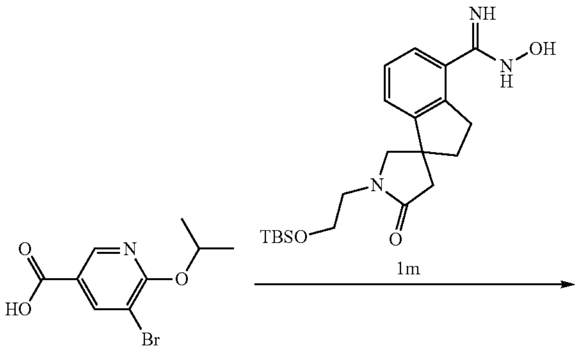

3c

Compound 3

Step 1

Compound 3a (200 mg, 862 μmol) and iodoisopropane (176 mg, 1.03 mmol) were dissolved in anhydrous toluene (3 mL), and silver carbonate (238 mg, 862 μmol) was added to the reaction solution, and the reaction solution was stirred at 50° C. for 16 hours. The reaction solution was concentrated under reduced pressure, and the crude product was diluted with water (20 mL), and the mixture was extracted with ethyl acetate (20 mL×1). The combined organic phases were washed with saturated brine (20 mL×2), dried with anhydrous sodium sulfate, filtered, and the filtrate was concentrated under reduced pressure to obtain the crude product of compound 3b.

MS-ESI calculated for $[M+H-^{i}Pr]^+$ 232 and 234, found 232 and 234.

Step 2

Compound 3b (260 mg, 949 μmol) was dissolved in anhydrous tetrahydrofuran (3 mL), anhydrous methanol (3 mL) and water (1 mL). Lithium hydroxide monohydrate (79.6 mg, 1.90 mmol) was added to the reaction solution, and the reaction solution was stirred at 25° C. for 12 hours. The reaction solution was concentrated under reduced pressure, and 1 N hydrochloric acid was added to the residue to adjust the pH to about 3. The reaction solution became turbid and was filtered to collect the filter cake. The filter cake was dried under reduced pressure to obtain the crude product of compound 3c.

MS-ESI calculated for $[M+H-^{i}Pr]^+$ 218 and 220, 218 and 220.

Step 3

Compound 3c (90.2 mg, 347 μmol) was dissolved in anhydrous N,N-dimethylformamide (5 mL), and then 1-hydroxybenzotriazole (56.3 mg, 416 μmol) and N-(3-dimethylaminopropyl)-N-ethylcarbodiimide (79.8 mg, 416 μmol) were added to the reaction solution. The reaction solution was stirred at 25° C. for 1 hour. 1m (140 mg, 347 μmol) was added to the reaction solution, and the reaction solution was stirred at 25° C. for 1 hour and stirred at 80° C. for 16 hours. The reaction solution was concentrated under reduced pressure, and the crude product was purified by high performance liquid chromatography {adjusted by hydrochloric acid, column type: 3_Phenomenex Luna C18 75*30 mm*3 μm; mobile phase: [water (0.05% HCl)-acetonitrile]; acetonitrile %: 66%-86%, 7 minutes} to obtain compound 3.

MS-ESI calculated for $[M+H]^+$ 513 and 515, found 513 and 515.

$^1H$ NMR (400 MHz, $CDCl_3$) δ=8.93 (d, J=2.1 Hz, 1H), 8.60-8.58 (m, 1H), 8.13-8.08 (m, 1H), 7.45-7.42 (m, 2H), 5.52-5.45 (m, 1H), 3.87 (t, J=5.0 Hz, 2H), 3.69-3.62 (m, 2H), 3.59-3.50 (m, 2H), 3.43-3.37 (m, 2H), 2.81 (d, J=16.9 Hz, 1H), 2.70 (d, J=16.9 Hz, 1H), 2.39-2.27 (m, 2H), 1.47 (d, J=6.2 Hz, 6H).

Embodiment 4

Compound 4

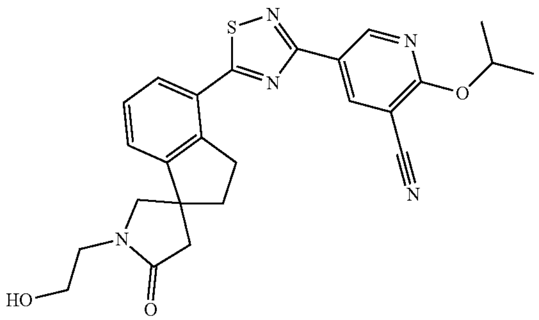

Synthetic Route:

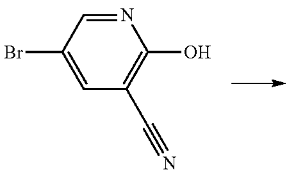

4a

-continued
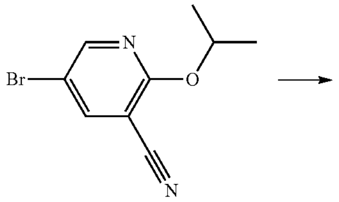
4b
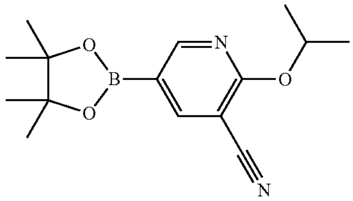
4c
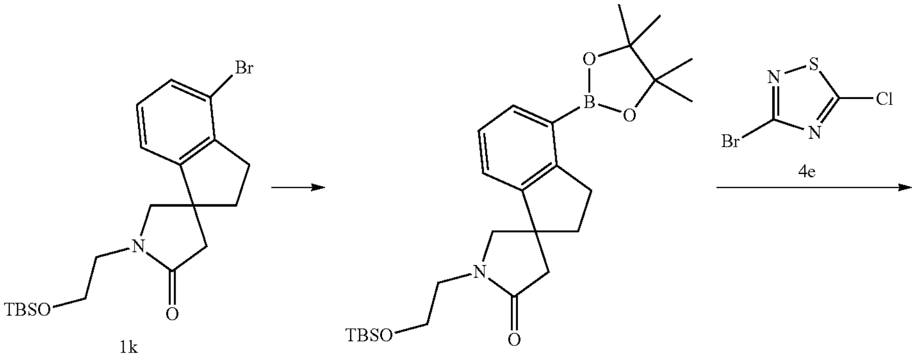
1k
4d
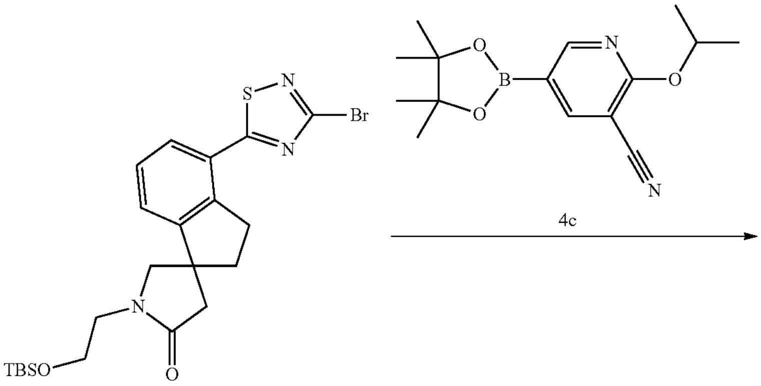
4f
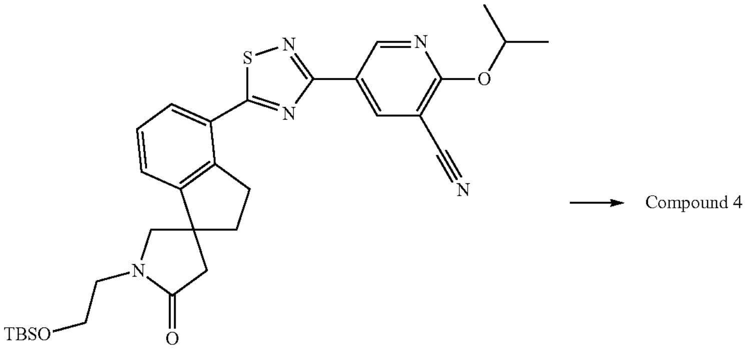
4g Step 1

Compound 4a (5 g, 25.1 mmol) and iodoisopropane (5.13 g, 30.2 mmol) were dissolved in anhydrous toluene (40 mL), and silver carbonate (3.46 g, 12.6 mmol) was added to the reaction solution, and the reaction solution was stirred at 50° C. for 16 hours. The reaction solution was concentrated under reduced pressure, and the crude product was diluted with water (100 mL), extracted with ethyl acetate (100 mL×1). The combined organic phases were washed with saturated brine (100 mL×2), dried with anhydrous sodium sulfate, filtered, and the filtrate was concentrated under reduced pressure to obtain the crude product of compound 4b.

MS-ESI calculated for $[M+H-^{i}Pr]^+$ 199 and 201, 199 and 201.

$^1H$ NMR (400 MHz, $CDCl_3$) δ=8.29 (d, J=2.5 Hz, 1H), 7.86 (d, J=2.5 Hz, 1H), 5.32-5.25 (m, 1H), 1.32 (d, J=6.2 Hz, 6H).

Step 2

Compound 4b (200 mg, 830 μmol), bis(pinacolato)diboron (253 mg, 996 μmol) and potassium acetate (163 mg, 1.66 mmol) were dissolved in anhydrous dioxane (3 mL). Under nitrogen protection, 1,1-bis(diphenylphosphino)ferrocene dichloropalladium (60.7 mg, 83.0 μmol) was added to the reaction solution, and the reaction solution was reacted at 120° C. for 3 hours. The reaction solution was concentrated under reduced pressure, and the crude product was diluted with water (20 mL), and the mixture was extracted with ethyl acetate (20 mL×1). The combined organic phases were washed with saturated brine (20 mL×1), dried with anhydrous sodium sulfate, and filtered. The filtrate was concentrated under reduced pressure, and the crude product was purified by column chromatography (5:1, petroleum ether/ethyl acetate, Rf=0.7) to obtain compound 4c.

MS-ESI calculated for $[M+H-^{i}Pr]^+$ 247, found 247.

1H NMR (400 MHz, CDCl3) δ=8.64 (d, J=1.8 Hz, 1H), 8.20 (d, J=1.8 Hz, 1H), 5.50-5.42 (m, 1H), 1.39 (d, J=6.1 Hz, 6H), 1.25 (s, 12H).

Step 3

Compound 1k (9 g, 21.2 mmol), bis(pinacolato)diboron (8.08 g, 31.8 mmol) and potassium acetate (4.16 g, 42.4 mmol) were dissolved in anhydrous dioxane (100 mL). Under nitrogen protection, 1,1-bis(diphenylphosphino)ferrocene dichloropalladium (1.55 g, 2.12 mmol) was added to the reaction solution, and the reaction solution was stirred at 80° C. for 12 hours. The reaction solution was concentrated under reduced pressure, and the crude product was diluted with water (200 mL), and the mixture was extracted with ethyl acetate (150 mL×2). The combined organic phases were washed with saturated brine (100 mL×2), dried with anhydrous sodium sulfate, and filtered. The filtrate was concentrated under reduced pressure, and the obtained crude product was purified by column chromatography (5:1, petroleum ether/ethyl acetate, Rf=0.13) to obtain compound 4d.

MS-ESI calculated for $[M+H]^+$ 472, found 472.

Step 4

Compound 4d (200 mg, 424 μmol), compound 4e (84.6 mg, 424 μmol) and potassium phosphate (180 mg, 848 μmol) were dissolved in anhydrous dioxane (5 mL) and water (1 mL). Under nitrogen atmosphere, 1,1-bis(diphenylphosphino)ferrocene dichloropalladium (31.0 mg, 42.4 μmol) was added to the reaction solution, and the reaction solution was stirred at 100° C. for 12 hours. The reaction solution was concentrated under reduced pressure, and the crude product was diluted with water (30 mL), and the mixture was extracted with ethyl acetate (30 mL×1). The combined organic phases were washed with saturated brine (30 mL×1), dried with anhydrous sodium sulfate, filtered, and the filtrate was concentrated under reduced pressure to obtain the crude product of compound 4f.

MS-ESI calculated for $[M+H]^+$ 508 and 510, found 508 and 510.

Step 5

Compound 4f (220 mg, 433 μmol), compound 4c (125 mg, 433 μmol) and potassium phosphate (184 mg, 865 μmol) were dissolved in anhydrous dioxane (5 mL) and water (1 mL). Under nitrogen protection, 1,1-bis(diphenylphosphino)ferrocene dichloropalladium (31.7 mg, 43.3 μmol) was added to the reaction solution, and the reaction solution was stirred at 80° C. for 12 hours. The reaction solution was concentrated under reduced pressure, and the crude product was diluted with water (30 mL), and the mixture was extracted with ethyl acetate (30 mL×1). The combined organic phases were washed with saturated brine (30 mL×1), dried with anhydrous sodium sulfate, and filtered. The filtrate was concentrated under reduced pressure, and the crude product was purified by column chromatography (2:1, petroleum ether/ethyl acetate, Rf=0.2) to obtain compound 4g.

MS-ESI calculated for $[M+H]^+$ 590, found 590.

Step 6

Compound 4g (113 mg, 192 μmol) was dissolved in ethyl acetate (1 mL), and hydrochloric acid/ethyl acetate (4 M, 1 mL) was added to the mixture, and the reaction solution was stirred at 20° C. for 1 hour. The reaction solution was concentrated under reduced pressure, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 56%-76%, 7 minutes) to obtain compound 4.

MS-ESI calculated for $[M+H]^+$ 476, found 476.

$^1H$ NMR (400 MHz, $CDCl_3$) δ=9.33 (d, J=2.3 Hz, 1H), 8.82 (d, J=2.3 Hz, 1H), 8.05-8.02 (m, 1H), 7.49-7.43 (m, 2H), 5.57-5.50 (m, 1H), 3.90-3.85 (m, 2H), 3.68-3.65 (m, 2H), 3.61-3.48 (m, 2H), 3.37 (t, J=7.2 Hz, 2H), 2.80 (d, J=16.8 Hz, 1H), 2.71 (d, J=16.8 Hz, 1H), 2.46-2.32 (m, 2H), 1.47 (d, J=6.2 Hz, 6H).

Embodiment 5
Compound 5
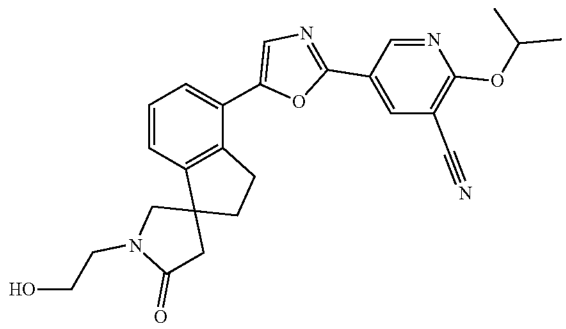
Synthetic Route:
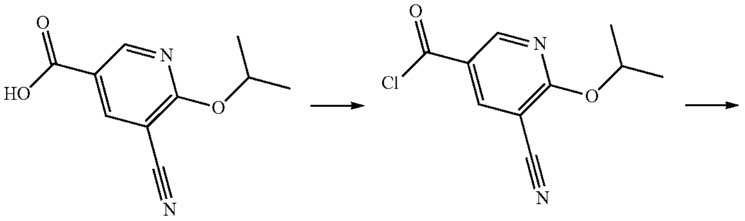
1d 5a
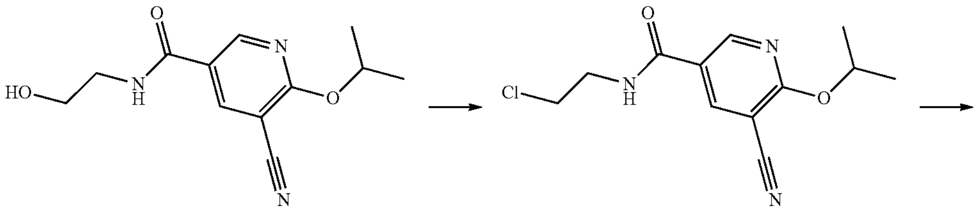
5b 5c
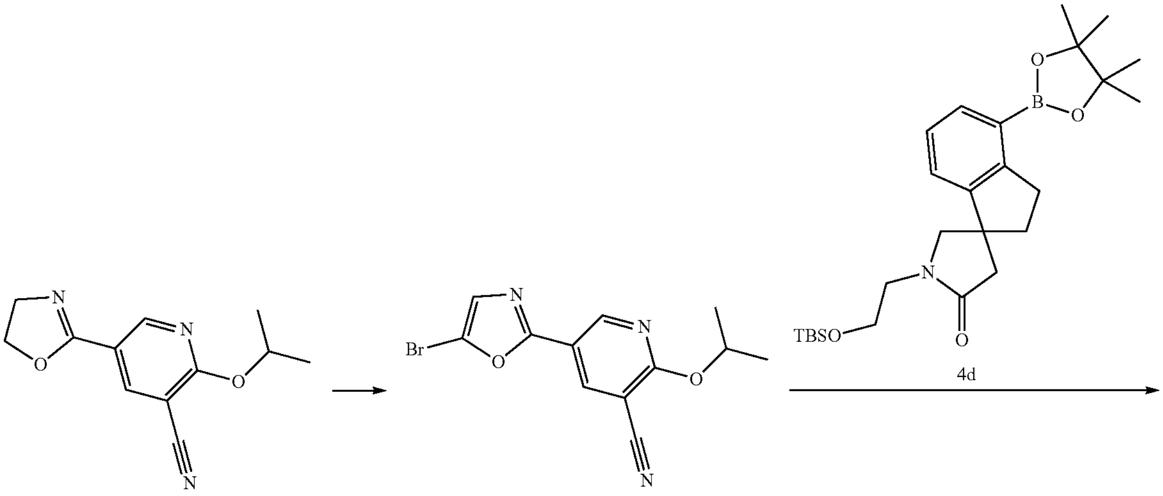
5d 5e 4d -continued

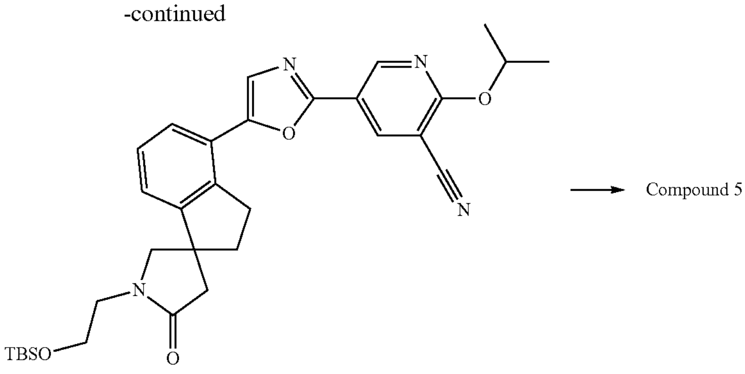

Compound 5

5f

Step 1

Compound 1d (500 mg, 2.42 mmol) was dissolved in anhydrous dichloromethane (5 mL), and then N,N-dimethylformamide (17.7 mg, 242 μmol) and oxalyl chloride (923 mg, 7.27 mmol) were added to the reaction solution, and the reaction solution was stirred at 25° C. for 2 hours. The reaction solution was concentrated under reduced pressure to remove the solvent to obtain the crude product of compound 5a.

Step 2

Compound 5a (520 mg, 2.31 mmol), 2-aminoethanol (212 mg, 3.47 mmol) were dissolved in anhydrous dichloromethane (5 mL), and N,N-diisopropylethylamine (598 mg, 4.63 mmol) was added to the reaction solution, and the reaction solution was stirred at 25° C. for 2 hours. The reaction solution was diluted with water (50 mL), extracted with dichloromethane (30 mL×2), and the organic phase was washed with water (50 mL×1), dried with anhydrous sodium sulfate, filtered, and the filtrate was concentrated under reduced pressure to obtain the crude product of compound 5b.

MS-ESI calculated for $[M+H]^+$ 250, found 250.

Step 3

Compound 5b (580 mg, 2.33 mmol) was dissolved in anhydrous dichloromethane (10 mL), and thionyl chloride (830 mg, 6.98 mmol) was added to the reaction solution, and the reaction solution was stirred at 25° C. for 12 hours. The reaction solution was concentrated under reduced pressure, and the crude product was purified by column chromatography (3:1, petroleum ether/ethyl acetate, Rf=0.3) to obtain compound 5c.

MS-ESI calculated for $[M+H]^+$ 268, found 268.

$^1$H NMR (400 MHz, $CDCl_3$) δ=8.68 (d, J=2.4 Hz, 1H), 8.24 (d, J=2.4 Hz, 1H), 6.52-6.42 (m, 1H), 5.45-5.38 (m, 1H), 3.77-3.72 (m, 2H), 3.70-3.65 (m, 2H), 1.35 (d, J=6.2 Hz, 6H).

Step 4

Compound 5c (300 mg, 1.12 mmol) was dissolved in anhydrous dichloromethane (3 mL), and triethylamine (340 mg, 3.36 mmol) was added to the reaction solution, and the reaction solution was stirred at 80° C. for 12 hours. The reaction solution was concentrated under reduced pressure, diluted with water (30 mL), extracted with dichloromethane (30 mL×2), and the organic phase was washed with water (30 mL×2), dried with anhydrous sodium sulfate, filtered, and the filtrate was concentrated under reduced pressure to obtain the crude product of compound 5d.

MS-ESI calculated for $[M+H]^+$ 232, found 232.

Step 5

Compound 5d (220 mg, 851 μmol) was dissolved in carbon tetrachloride (5 mL), and then N-bromosuccinimide (508 mg, 2.85 mmol) and azodiisobutyronitrile (7.81 mg, 47.6 μmol) were added to the reaction solution, and the reaction solution was stirred at 80° C. for 12 hours. The reaction solution was concentrated under reduced pressure, and the crude product was purified by column chromatography (3:1, petroleum ether/ethyl acetate, Rf=0.31) to obtain compound 5e.

MS-ESI calculated for $[M+H]^+$ 308 and 310, found 308 and 310.

Step 6

Compound 5e (90.2 mg, 293 μmol), compound 4d (138 mg, 293 μmol) and potassium phosphate (124 mg, 585 μmol) were dissolved in anhydrous dioxane (3 mL). Under nitrogen protection, 1,1-bis(diphenylphosphino)ferrocene dichloropalladium (21.4 mg, 29.3 μmol) was added to the reaction solution, and the reaction solution was stirred at 80° C. for 12 hours. The reaction solution was concentrated under reduced pressure, and the crude product was diluted with water (20 mL), and the mixture was extracted with ethyl acetate (20 mL×1). The combined organic phases were washed with saturated brine (20 mL×1), dried with anhydrous sodium sulfate, and filtered. The filtrate was concentrated under reduced pressure, and the obtained crude product was purified by thin layer chromatographic plate (1:1, petroleum ether/ethyl acetate, Rf=0.13) to obtain compound 5f.

MS-ESI calculated for $[M+H]^+$ 573, found 573.

Step 7

Compound 5f (100 mg, 175 μmol) was dissolved in ethyl acetate (1 mL), and hydrochloric acid/ethyl acetate (4 M, 1.2 mL) was added to the mixture, and the reaction solution was stirred at 20° C. for 1 hour. The reaction solution was concentrated under reduced pressure, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 45%-65%, 7 minutes} to obtain compound 5.

MS-ESI calculated for $[M+H]^+$ 459, found 459.

$^1$H NMR (400 MHz, $CDCl_3$) δ=9.05 (d, J=2.4 Hz, 1H), 8.52 (d, J=2.3 Hz, 1H), 7.68 (d, J=7.6 Hz, 1H), 7.41-7.36 (m,

2H), 7.29 (d, J=7.7 Hz, 1H), 5.55-5.48 (m, 1H), 3.89-3.84 (m, 2H), 3.68-3.61 (m, 2H), 3.58-3.51 (m, 2H), 3.18 (t, J=7.1 Hz, 2H), 2.82-2.76 (m, 1H), 2.71-2.65 (m, 2H), 2.41-2.29 (m, 2H), 1.46 (d, J=6.2 Hz, 6H).
Embodiment 6
Compound 6
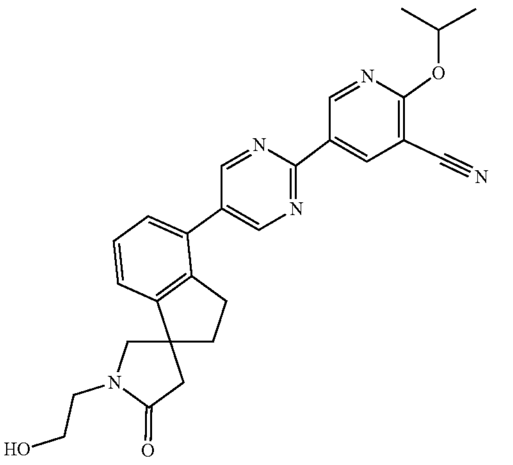
Synthetic Route:
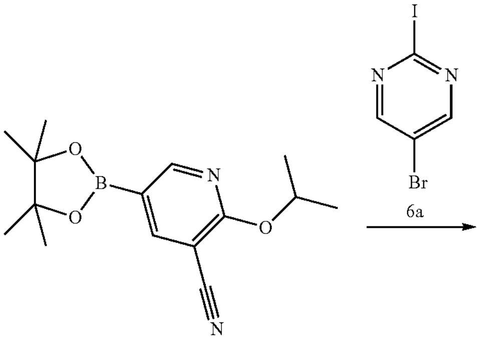
6a
4c
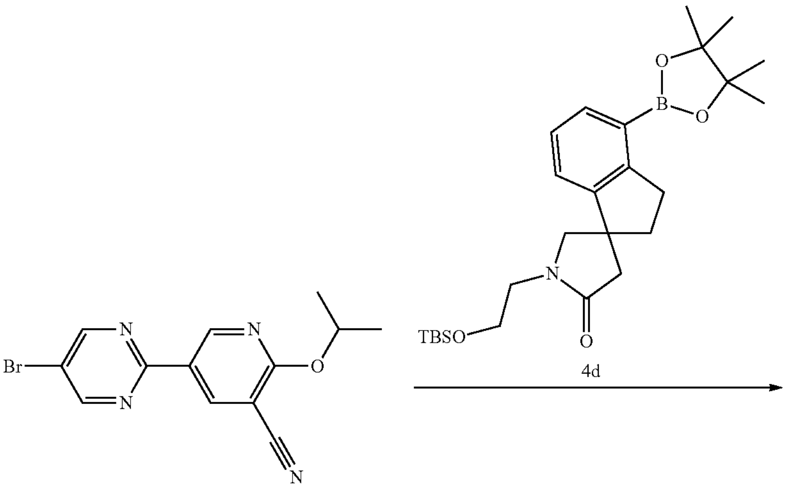
4d
6b -continued

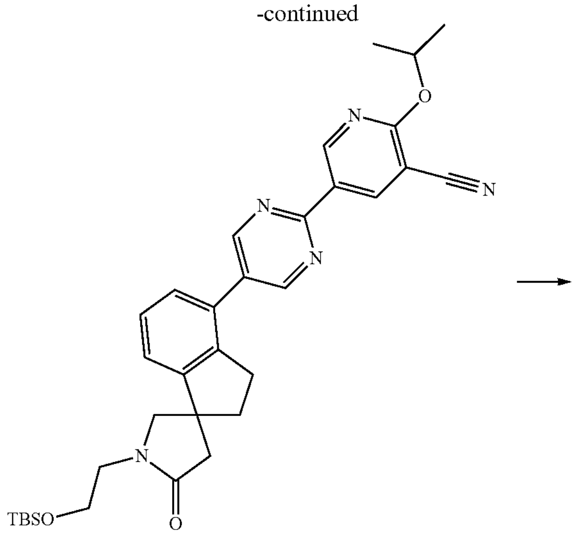

Compound 6

6c

Step 1

Compound 4c (200 mg, 694 μmol), compound 6a (198 mg, 694 μmol) and potassium phosphate (295 mg, 1.39 mmol) were dissolved in anhydrous dioxane (4 mL) and water (1 mL). Under nitrogen protection, 1,1-bis(diphenylphosphino)ferrocene dichloropalladium (51.0 mg, 69.7 μmol) was added to the reaction solution, and the reaction solution was stirred at 80° C. for 12 hours. The reaction solution was concentrated under reduced pressure, and the crude product was diluted with water (30 mL), and the mixture was extracted with ethyl acetate (30 mL×2). The combined organic phases were washed with saturated brine (30 mL×1), dried with anhydrous sodium sulfate, filtered, and the filtrate was concentrated under reduced pressure to obtain the crude product of compound 6b.

MS-ESI calculated for $[M+H]^+$ 319 and 321, found 319 and 321.

Step 2

Compound 6b (102 mg, 318 μmol), compound 4d (150 mg, 318 μmol) and potassium phosphate (135 mg, 636 μmol) were dissolved in anhydrous dioxane (3 mL) and water (1 mL). Under nitrogen protection, 1,1-bis(diphenylphosphino)ferrocene dichloropalladium (23.3 mg, 31.8 μmol) was added to the reaction solution, and the reaction solution was stirred at 80° C. for 12 hours. The reaction solution was concentrated under reduced pressure, and the crude product was diluted with water (30 mL), and the mixture was extracted with ethyl acetate (30 mL×1). The combined organic phases were washed with saturated brine (30 mL×1), dried with anhydrous sodium sulfate, and filtered. The filtrate was concentrated under reduced pressure, and the crude product was purified by column chromatography (1:1, petroleum ether/ethyl acetate, Rf=0.25) to obtain compound 6c.

MS-ESI calculated for $[M+H]^+$ 584, found 584.

Step 3

Compound 6c (86 mg, 147 μmol) was dissolved in ethyl acetate (1 mL), and hydrochloric acid/ethyl acetate (4 M, 1 mL) was added to the mixture, and the reaction solution was stirred at 20° C. for 1 hour. The reaction solution was concentrated under reduced pressure, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 50%-70%, 7 minutes} to obtain compound 6.

MS-ESI calculated for $[M+H]^+$ 470, found 470.

$^1H$ NMR (400 MHz, $CDCl_3$) δ=9.42 (d, J=2.1 Hz, 1H), 8.95 (d, J=2.1 Hz, 1H), 8.88 (s, 2H), 7.45-7.37 (m, 2H), 7.32 (d, J=7.1 Hz, 1H), 5.58-5.51 (m, 1H), 3.91-3.83 (m, 2H), 3.74-3.64 (m, 2H), 3.60-3.49 (m, 2H), 3.09-3.02 (m, 2H), 2.86-2.78 (m, 1H), 2.74-2.67 (m, 1H), 2.66-2.63 (m, 1H), 2.34-2.22 (m, 2H), 1.46 (d, J=6.1 Hz, 6H).

Embodiment 7

Compound 7

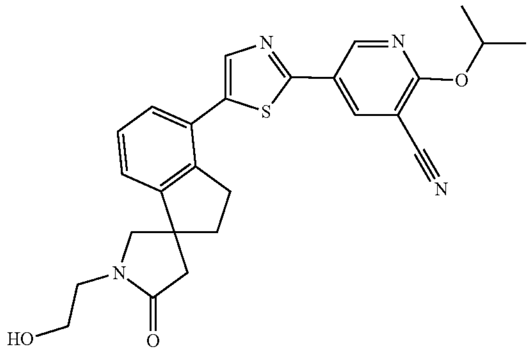

Synthetic Route:

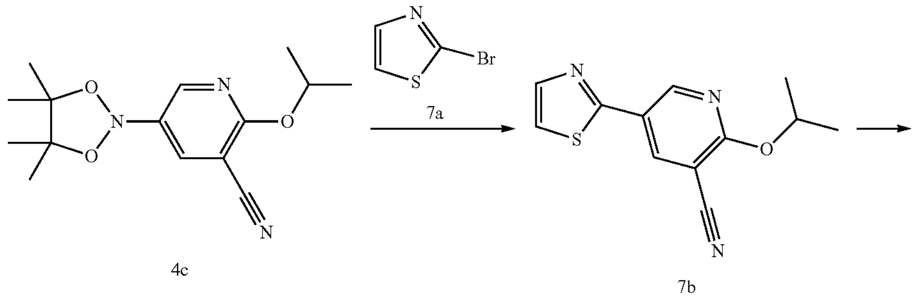

4c 7b

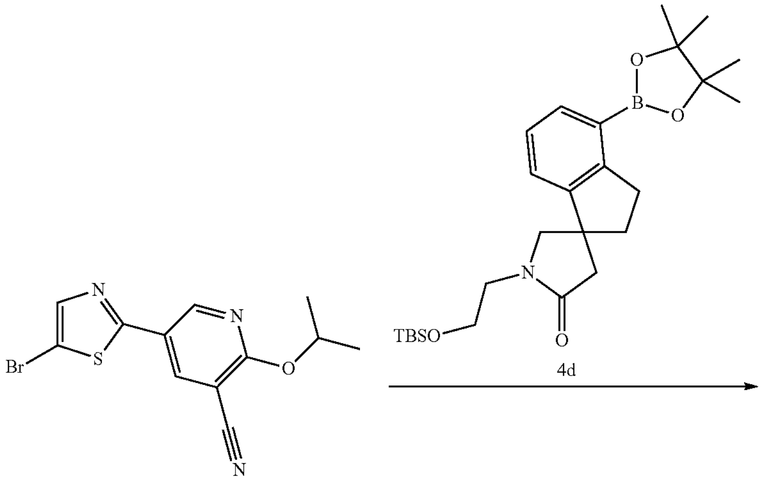

7c

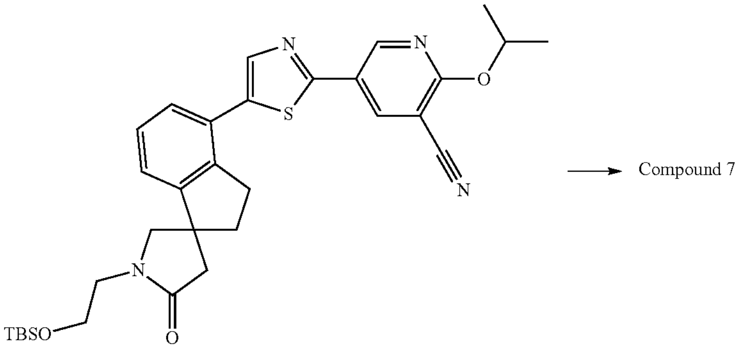

7d

Step 1

Compound 4c (300 mg, 1.04 mmol), compound 7a (171 mg, 1.04 mmol) and potassium phosphate (442 mg, 2.08 mmol) were dissolved in anhydrous dioxane (5 mL) and water (1 mL). Under nitrogen protection, 1,1-bis(diphenylphosphino)ferrocene dichloropalladium (76.2 mg, 104 μmol) was added to the reaction solution, and the reaction solution was stirred at 80° C. for 12 hours. The reaction solution was diluted with water (50 mL), and the mixture was extracted with ethyl acetate (50 mL×2). The combined organic phases were washed with saturated brine (50 mL×2), dried with anhydrous sodium sulfate, and filtered. The filtrate was concentrated under reduced pressure, and the crude product was purified by column chromatography (5:1, petroleum ether/ethyl acetate, Rf=0.53) to obtain compound 7b.

MS-ESI calculated for $[M+H]^+$ 246, found 246.

Step 2

Compound 7b (92 mg, 375 μmol) was dissolved in anhydrous N,N-dimethylformamide (3 mL), and N-bromosuccinimide (134 mg, 750 μmol) was added to the reaction solution at 0° C., and the reaction solution was stirred at 60° C. for 3 hours. The reaction solution was diluted with water (30 mL), and the mixture was extracted with ethyl acetate (30 mL×2). The combined organic phases were washed with saturated brine (30 mL×2), dried with anhydrous sodium sulfate, and filtered. The filtrate was concentrated under reduced pressure, and the crude product was purified by column chromatography (5:1, petroleum ether/ethyl acetate, Rf=0.64) to obtain compound 7c.

MS-ESI calculated for $[M+H]^+$ 324 and 326, found 324 and 326.

Step 3

Compound 7c (62.0 mg, 191 μmol), compound 4d (90.2 mg, 191 μmol) and potassium phosphate (81.2 mg, 382 μmol) were dissolved in anhydrous dioxane (3 mL) and water (1 mL). Under nitrogen protection, 1,1-bis(diphenylphosphino)ferrocene dichloropalladium (14.0 mg, 19.1 μmol) was added to the reaction solution, and the reaction solution was stirred at 80° C. for 12 hours. The reaction solution was concentrated under reduced pressure to remove the solvent, and the crude product was diluted with water (15 mL), and the mixture was extracted with ethyl acetate (15 mL×2). The combined organic phases were washed with saturated brine (20 mL×2), dried with anhydrous sodium sulfate, and filtered. The filtrate was concentrated under reduced pressure, and the crude product was purified by thin layer chromatographic plate (1:1, petroleum ether/ethyl acetate, Rf=0.40) to obtain compound 7d.

MS-ESI calculated for $[M+H]^+$ 589, found 589.

Step 4

Compound 7d (102 mg, 173 μmol) was dissolved in ethyl acetate (1 mL), and hydrochloric acid/ethyl acetate (4 M, 1 mL) was added to the mixture, and the reaction solution was stirred at 20° C. for 1 hour. The reaction solution was concentrated under reduced pressure, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 52%-72%, 7 minutes} to obtain compound 7.

MS-ESI calculated for $[M+H]^+$ 475, found 475.

$^1$H NMR (400 MHz, $CDCl_3$) δ=8.90 (s, 1H), 8.46 (s, 1H), 7.95 (s, 1H), 7.45 (d, J=6.8 Hz, 1H), 7.38-7.28 (m, 2H), 5.54-5.46 (m, 1H), 3.86 (br s, 2H), 3.73-3.62 (m, 2H), 3.60-3.48 (m, 2H), 3.20-3.10 (m, 2H), 2.84-2.75 (m, 1H), 2.73-2.63 (m, 1H), 2.38-2.23 (m, 2H), 1.45 (d, J=6.1 Hz, 6H).

Embodiment 8

Compound 8

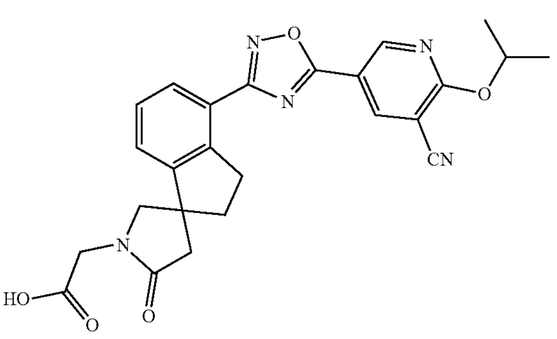

Synthetic Route:

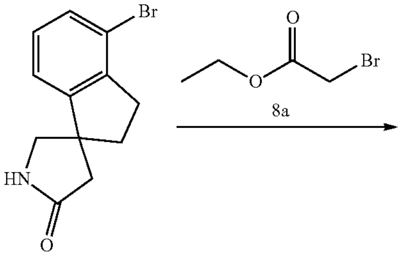

8a

1i

-continued

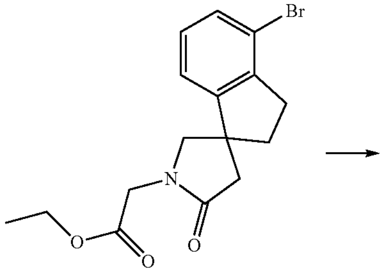

8b

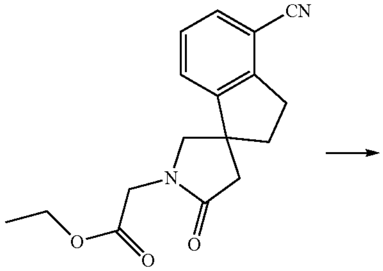

8c

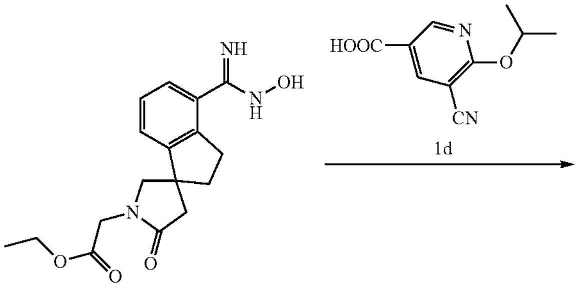

1d

8d

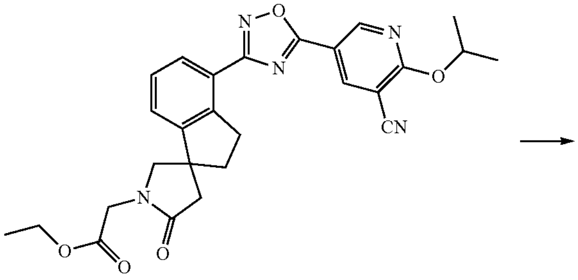

8e

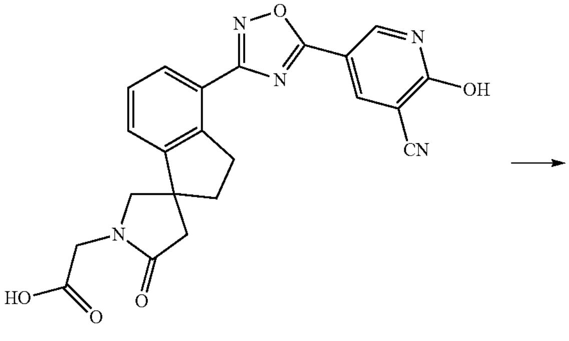

8f

-continued

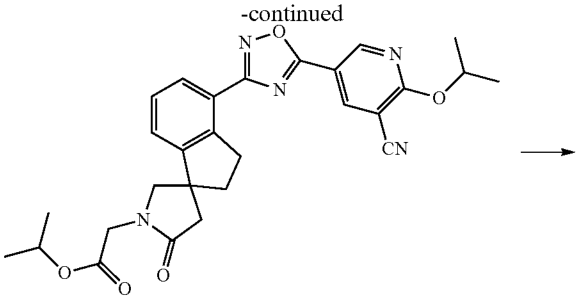

8g

Compound 8

Step 1

Compound 1i (500 mg, 1.88 mmol) was dissolved in anhydrous tetrahydrofuran (20 mL), and potassium tert-butoxide (316 mg, 2.82 mmol) was added to the mixture at 0° C. The reaction solution was stirred at 0° C. for 0.5 hours, and compound 8a (941 mg, 5.64 mmol) was added to the mixture at 0° C., and the reaction solution was stirred at 20° C. for 2 hours. The reaction solution was added with 30 mL of water to dilute, extracted with ethyl acetate (30 mL*3). The organic phases were combined, and the organic phases were washed with 30 mL of water and 30 mL of saturated brine in turn, dried with anhydrous sodium sulfate. The crude product was purified by column chromatography (1:1, petroleum ether/ethyl acetate, Rf=0.39) to obtain compound 8b.

MS-ESI calculated for $[M+H]^+$ 352 and 354, found 352 and 354.

$^1$H NMR (400 MHz, $CDCl_3$) δ=7.31 (d, J=7.8 Hz, 1H), 7.19 (d, J=7.5 Hz, 1H), 7.07-7.01 (m, 1H), 4.14 (q, J=7.2 Hz, 2H), 4.06-4.03 (m, 2H), 3.53 (d, J=9.4 Hz, 1H), 3.47 (d, J=9.4 Hz, 1H), 2.90 (t, J=7.2 Hz, 2H), 2.64 (d, J=16.9 Hz, 1H), 2.54 (d, J=16.9 Hz, 1H), 2.31-2.22 (m, 1H), 2.18-2.09 (m, 1H), 1.22 (t, J=7.2 Hz, 3H).

Step 2

Compound 8b (467 mg, 1.33 mmol) was dissolved in anhydrous N,N-dimethylformamide (3 mL), and then zinc cyanide (234 mg, 1.99 mmol), tris(dibenzylideneacetone) dipalladium (60.7 mg, 66.3 μmol) and 2-di-tert-butylphosphino-2',4',6'-triisopropylbiphenyl (63.2 mg, 133 μmol) were added to the mixture. Under nitrogen protection, the reaction solution was stirred at 90° C. for 12 hours, the reaction solution was concentrated, and the crude product was purified by column chromatography (5:1-3:1, petroleum ether/ethyl acetate, Rf=0.24) to obtain compound 8c.

MS-ESI calculated for $[M+H]^+$ 299, found 299.

Step 3

Hydroxylamine hydrochloride (143 mg, 2.07 mmol) and triethylamine (209 mg, 2.07 mmol) were dissolved in anhydrous ethanol (5 mL), and compound 8c (206 mg, 690 μmol) was added to the mixture under nitrogen protection. The reaction solution was stirred at 80° C. for 4 hours under nitrogen protection, and the reaction solution was concentrated to remove the solvent. The crude product was purified by high performance liquid chromatography {neutral condition, column type: Waters Xbridge C18 150*50 mm*10 μm; mobile phase: [water (10 mM ammonium bicarbonate)-acetonitrile]; B %: 8%-38%, 11.5 minutes} to obtain compound 8d.

MS-ESI calculated for $[M+H]^+$ 332, found 332.

Step 4

Compound 1d (79.6 mg, 386 μmol) was dissolved in anhydrous N,N-dimethylformamide (10 mL), and then 1-hydroxybenzotriazole (62.6 mg, 463 μmol) and 1-(3-dimethylaminopropyl)-3-ethylcarbodiimide hydrochloride (88.8 mg, 463 μmol) were added to the mixture. The reaction solution was stirred at 25° C. for 1 hour, and compound 8d (128 mg, 386 μmol) was added to the reaction solution. The reaction solution was stirred at 25° C. for 2 hours, and the reaction solution was further stirred at 80° C. for 8 hours. The reaction solution was added with 30 mL of water, extracted with dichloromethane (30 mL*2), and the organic phases were combined. The organic phases were washed with 20 mL of water and 20 mL of saturated brine, dried with anhydrous sodium sulfate, and concentrated to obtain compound 8e.

MS-ESI calculated for $[M+H]^+$ 502, found 502.

Step 5

Compound 8e (188 mg, 375 μmol) was dissolved in anhydrous tetrahydrofuran (8 mL) and anhydrous methanol (4 mL), and then a water (2 mL) solution dissolved with lithium hydroxide monohydrate (62.9 mg, 1.50 mmol) was added to the mixture, and the reaction solution was stirred at 25° C. for 12 hours. The reaction solution was concentrated to remove the solvent, and the crude product was purified by high performance liquid chromatography {hydrochloric acid condition, column type: 3_Phenomenex Luna C18 75*30 mm*3 μm; mobile phase: [water (0.05% HCl)-acetonitrile]; B %: 20%-40%, 8 minutes} to obtain compound 8f.

MS-ESI calculated for $[M+H]^+$ 432, found 432.

$^1$H NMR (400 MHz, DMSO-$d_6$) δ=13.48 (br s, 1H), 12.85 (br s, 1H), 8.80 (d, J=2.6 Hz, 1H), 8.71 (d, J=2.7 Hz, 1H), 8.00-7.96 (m, 1H), 7.63 (d, J=7.3 Hz, 1H), 7.49-7.43 (m, 1H), 4.08-3.97 (m, 2H), 3.56 (s, 2H), 3.27 (t, J=7.2 Hz, 2H), 2.68 (d, J=16.5 Hz, 1H), 2.54 (d, J=16.5 Hz, 1H), 2.38-2.28 (m, 1H), 2.23-2.13 (m, 1H).

Step 6

Compound 8f (38.4 mg, 88.9 μmol) and 2-iodopropane (45.4 mg, 267 μmol) were dissolved in anhydrous toluene (3 mL), and silver carbonate (24.5 mg, 88.9 μmol) was added to the mixture, and the reaction solution was stirred at 50° C. for 16 hours. The reaction solution was concentrated under reduced pressure, and the crude product was purified by thin layer chromatography (2:1, petroleum ether/ethyl acetate, Rf=0.15) to obtain compound 8g.

MS-ESI calculated for $[M+H]^+$ 516, found 516.

Step 7

Compound 8g (22.0 mg, 42.7 μmol) was dissolved in anhydrous tetrahydrofuran (2 mL), and a solution of sodium hydroxide (6.83 mg, 170 μmol) in water (0.5 mL) was added to the mixture, and the reaction solution was stirred at 20° C. for 12 hours. The reaction solution was concentrated, and the crude product was purified by high performance liquid chromatography {hydrochloric acid condition, column type: 3_Phenomenex Luna C18 75*30 mm*3 μm; mobile phase:

[water (0.05% HCl)-acetonitrile]; acetonitrile %: 52%-72%, 7 minutes} to obtain compound 8.

MS-ESI calculated for $[M+H]^+$ 474, found 474.

$^1H$ NMR (400 MHz, $CDCl_3$) δ=9.15 (d, J=2.3 Hz, 1H), 8.64 (d, J=2.3 Hz, 1H), 8.09 (d, J=7.5 Hz, 1H), 7.51 (d, J=7.6 Hz, 1H), 7.43 (t, J=7.6 Hz, 1H), 5.62-5.51 (m, 1H), 4.30-4.15 (m, 2H), 3.71 (d, J=9.4 Hz, 1H), 3.63 (d, J=9.4 Hz, 1H), 3.38 (t, J=6.9 Hz, 2H), 2.82 (d, J=17.0 Hz, 1H), 2.72 (d, J=17.0 Hz, 1H), 2.48-2.23 (m, 2H), 1.48 (d, J=6.2 Hz, 6H).

Embodiment 9

Compound 9

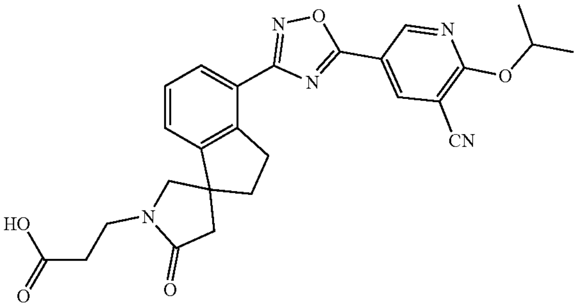

Synthetic Route:

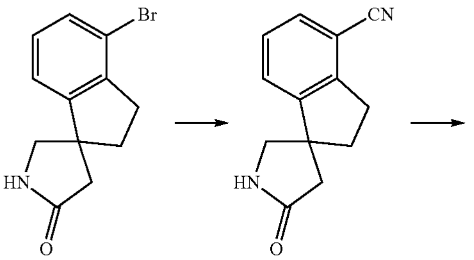

1i 9a

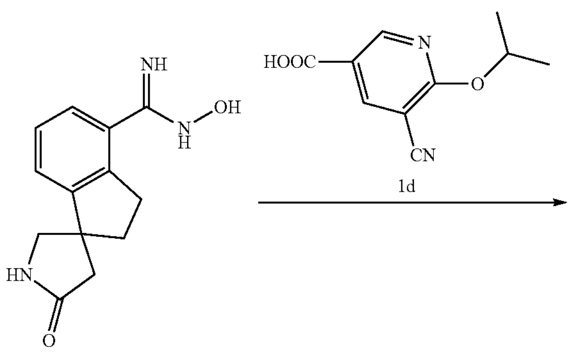

1d

9b

-continued

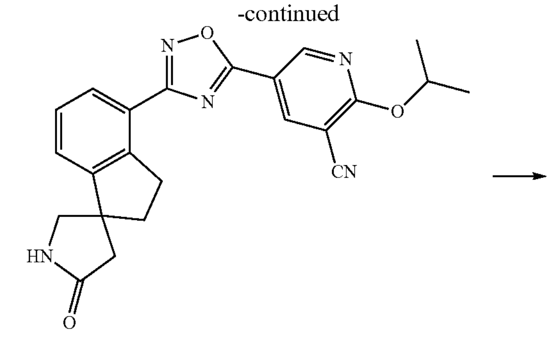

9c

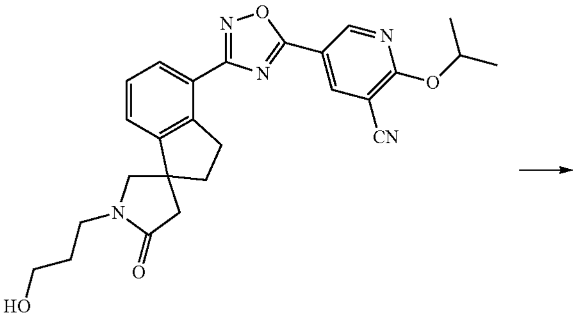

9d

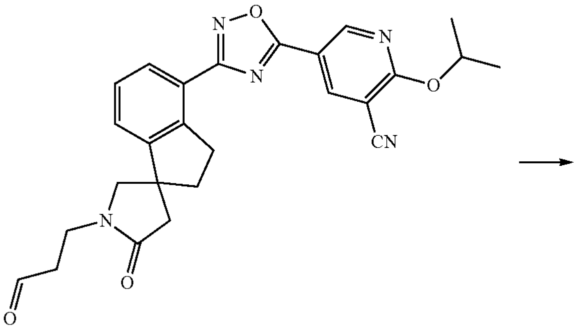

9e

Compound 9

Step 1

Compound 1i (5.00 g, 18.8 mmol) was dissolved in anhydrous N,N-dimethylformamide (50 mL), and then zinc cyanide (3.31 g, 28.2 mmol), tris(dibenzylideneacetone) dipalladium (516 mg, 564 μmol) and 2-di-tert-butylphosphino-2',4',6'-triisopropylbiphenyl (537 mg, 1.13 mmol) were added to the mixture. Under nitrogen protection, the reaction solution was stirred at 90° C. for 12 hours, diluted with 100 mL of water, extracted with ethyl acetate (60 mL*3). The organic phases were combined, and the organic phases were washed with 50 mL of water and 50 mL of saturated brine, dried with anhydrous sodium sulfate and concentrated. 50 mL of ethanol was added to the crude product, and the reaction solution was stirred at 20° C. for 12 hours, filtered, and the filter cake was dried under reduced pressure to obtain compound 9a.

MS-ESI calculated for $[M+H]^+$ 213, found 213.

$^1H$ NMR (400 MHz, $CDCl_3$) δ=7.53 (d, J=7.8 Hz, 1H), 7.50 (d, J=7.8 Hz, 1H), 7.34 (t, J=7.6 Hz, 1H), 5.97 (br s, 1H), 3.55-3.47 (m, 2H), 3.16 (t, J=7.2 Hz, 2H), 2.65-2.51 (m, 2H), 2.42-2.25 (m, 2H).

Step 2

Compound 9a (100 mg, 471 μmol) was dissolved in anhydrous ethanol (2 mL), and then hydroxylamine hydrochloride (98.2 mg, 1.41 mmol) and triethylamine (143 mg, 1.41 mmol) were added to the mixture under nitrogen conditions. The reaction solution was stirred at 80° C. for 4 hours under nitrogen protection, and the reaction solution was concentrated. 5 mL of ethyl acetate was added to the crude product, and the reaction solution was stirred at 20° C. for 12 hours, filtered, and the filter cake was dried under reduced pressure to obtain compound 9b.

MS-ESI calculated for $[M+H]^+$ 246, found 246.

Step 3

Compound 1d (123 mg, 594 μmol) was dissolved in anhydrous N,N-dimethylformamide (10 mL), and then 1-hydroxybenzotriazole (107 mg, 793 μmol) and 1-(3-dimethylaminopropyl)-3-ethylcarbodiimide hydrochloride (152 mg, 793 μmol) were added to the mixture. The reaction solution was stirred at 25° C. for 1 hour, and compound 9b (162 mg, 660 μmol) was added to the reaction solution. The reaction solution was stirred at 25° C. for 2 hours, and the reaction solution was further stirred at 80° C. for 8 hours. The reaction solution was added with 20 mL of water, extracted with ethyl acetate (30 mL*2). The organic phases were combined, and the organic phases were washed with 20 mL of water and 20 mL of saturated brine, and dried with anhydrous sodium sulfate. The crude product was purified by thin layer chromatography (0:1, petroleum ether/ethyl acetate, Rf=0.42) to obtain compound 9c.

MS-ESI calculated for $[M+H]^+$ 416, found 416.

Step 4

Compound 9c (100 mg, 241 μmol) was dissolved in anhydrous tetrahydrofuran (10 mL), and potassium tert-butoxide (35.1 mg, 313 μmol) was added to the mixture at 0° C. The reaction solution was stirred at 0° C. for 0.5 hours, and 3-bromopropanol (100 mg, 722 μmol) was added to the mixture at 0° C., and the reaction solution was stirred at 20° C. for 2 hours. The reaction solution was added with 30 mL of water, extracted with ethyl acetate (50 mL*3). The organic phases were combined, and the organic phases were washed with 30 mL of water and 30 mL of saturated brine, and dried with anhydrous sodium sulfate. The crude product was purified by thin layer chromatography (0:1, petroleum ether/ethyl acetate, Rf=0.46) to obtain compound 9d.

MS-ESI calculated for $[M+H]^+$ 474, found 474.

Step 5

Compound 9d (31.0 mg, 65.6 μmol) was dissolved in anhydrous dichloromethane (2 mL), and Dess-Martin periodinane (46.1 mg, 109 μmol) was added to the mixture. The reaction solution was stirred at 20° C. for 2 hours, and saturated 10% sodium bicarbonate solution (10 mL) was added to the reaction solution, and the mixture was extracted with dichloromethane (10 mL*2). The organic phases were combined, and the organic phases were washed with 10 mL of water and 10 mL of saturated brine, dried with anhydrous sodium sulfate and concentrated to obtain compound 9e.

MS-ESI calculated for $[M+H]^+$ 472, found 472.

Step 6

Compound 9e (35.0 mg, 74.2 μmol) was dissolved in anhydrous tetrahydrofuran (1 mL) and tert-butanol (1 mL), and then 2-methyl-2-butene (52.0 mg, 742 μmol), a solution of disodium hydrogen phosphate (105 mg, 742 μmol) and sodium chlorite (10.0 mg, 111 μmol) in water (1 mL) were added to the mixture. The reaction solution was stirred at 20° C. for 1 hour, added with water (10 mL), extracted with dichloromethane (10 mL*2). The organic phases were combined, and the organic phases were washed with 10 mL of water and 10 mL of saturated brine, dried with anhydrous sodium sulfate. The crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 50%-70%, 7 minutes} to obtain compound 9.

MS-ESI calculated for $[M+H]^+$ 488, found 488.

$^1H$ NMR (400 MHz, $CDCl_3$) δ=9.14 (d, J=2.3 Hz, 1H), 8.63 (d, J=2.3 Hz, 1H), 8.07 (d, J=6.2 Hz, 1H), 7.46-7.34 (m, 2H), 5.63-5.51 (m, 1H), 3.74-3.56 (m, 4H), 3.42-3.30 (m, 2H), 2.80-2.60 (m, 4H), 2.40-2.18 (m, 2H), 1.48 (d, J=6.1 Hz, 6H).

Embodiment 10

Compound 10

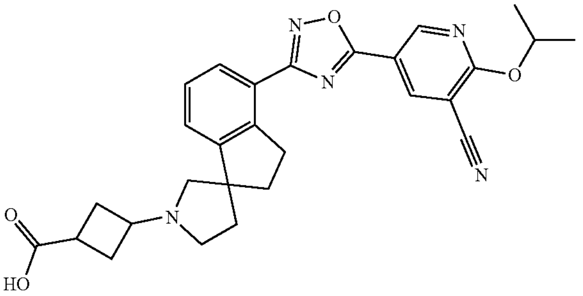

Synthetic Route:

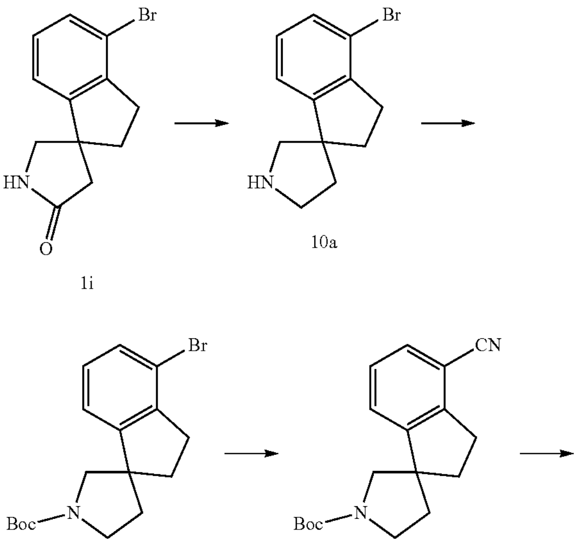

1i 10a 10b 10c

-continued

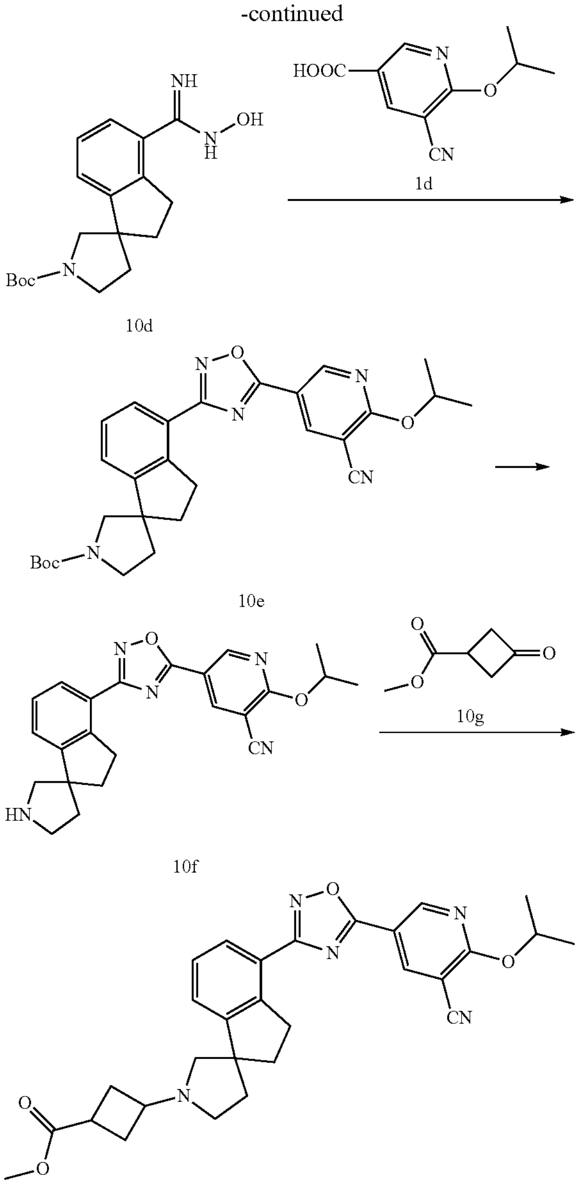

10d

10e

10f

10h

Compound 10

Step 1

Compound 1i (2.00 g, 7.52 mmol) was dissolved in anhydrous tetrahydrofuran (20 mL), and lithium aluminum hydride (570 mg, 15.0 mmol) was slowly added to the reaction solution in batches, and the reaction solution was stirred at 70° C. for 3 hours. The reaction solution was quenched by adding saturated ammonium chloride solution (50 mL), filtered, and the filtrate was collected and concentrated under reduced pressure. The residue was diluted with water (100 mL), and the mixture was extracted with ethyl acetate (100 mL×2). The combined organic phases were washed with saturated brine (100 mL×2), dried with anhydrous sodium sulfate, filtered, and the filtrate was concentrated under reduced pressure to obtain the crude product of compound 10a.

MS-ESI calculated for $[M+H]^+$ 252 and 254, found 252 and 254.

Step 2

Compound 10a (1.22 g, 4.84 mmol) was dissolved in anhydrous dichloromethane (20 mL), and then di-tert-butyl dicarbonate (1.27 g, 5.81 mmol) and triethylamine (1.18 g, 11.6 mmol) were added to the mixture. The reaction solution was stirred at 25° C. for 2 hours. The reaction solution was concentrated, and the crude product was purified by silica gel column chromatography (5:1, petroleum ether/ethyl acetate, Rf=0.7) to obtain compound 10b.

MS-ESI calculated for $[M+H-^tBu]^+$ 296 and 298, found 296 and 298.

Step 3

Compound 10b (1.44 g, 4.09 mmol), zinc cyanide (720 mg, 6.13 mmol) and 2-dicyclohexylphosphino-2,4,6-triisopropylbiphenyl (156 mg, 327 μmol) were dissolved in anhydrous N,N-dimethylformamide (20 mL), and tris (dibenzylideneacetone)dipalladium (150 mg, 164 μmol) was added to the mixture under nitrogen protection. The reaction solution was stirred at 90° C. for 12 hours. The reaction solution was diluted with water (100 mL), and the mixture was extracted with ethyl acetate (100 mL×2). The combined organic phases were washed with saturated brine (100 mL×2), dried with anhydrous sodium sulfate, and filtered. The filtrate was concentrated under reduced pressure, and the crude product was purified by silica gel column chromatography (5:1, petroleum ether/ethyl acetate, Rf=0.25) to obtain compound 10c.

MS-ESI calculated for $[M+H-^tBu]^+$ 243, found 243.

Step 4

Compound 10c (720 mg, 2.41 mmol) was dissolved in anhydrous ethanol (10 mL), and then hydroxylamine hydrochloride (502 mg, 7.22 mmol) and triethylamine (731 mg, 7.22 mmol) were added to the mixture. The reaction solution was stirred at 80° C. for 3 hours. The reaction solution was concentrated under reduced pressure, diluted by adding water (25 mL) to the residue. The reaction solution became turbid, filtered, and the filter cake was dried under vacuum to obtain the crude product of compound 10d.

MS-ESI calculated for $[M+H]^+$ 332, found 332.

Step 5

Compound 1d (790 mg, 3.83 mmol) was dissolved in anhydrous N,N-dimethylformamide (10 mL), and then 1-hydroxybenzotriazole (621 mg, 4.60 mmol) and 1-(3-dimethylaminopropyl)-3-ethylcarbodiimide hydrochloride (882 mg, 4.60 mmol) were added to the mixture. The reaction solution was stirred at 25° C. for 1 hour, and compound 10d (1.27 g, 3.83 mmol) was added to the reaction solution. The reaction solution was stirred at 25° C. for 2 hours, and the reaction solution was further stirred at 80° C. for 8 hours. The reaction solution was added with 80 mL of water, extracted with ethyl acetate (60 mL*3). The organic phases were combined, and the organic phases were washed with saturated brine (60 mL*3), dried with anhydrous sodium sulfate, and concentrated to obtain compound 10e.

MS-ESI calculated for $[M+H-^tBu]^+$ 446, found 446.

Step 6

Compound 10e (1.93 mg, 2.74 mmol) was dissolved in ethyl acetate (30 mL), and ethyl acetate hydrochloride (4 M, 6.85 mL) was added to the mixture. The reaction solution was stirred at 25° C. for 1 hour, filtered. The filter cake was collected, and ethyl acetate (50 mL) was added to the filter cake, and the mixture was stirred at 20° C. for 12 hours, filtered. The filter cake was dried under reduced pressure to obtain a hydrochloride salt of compound 10f.

MS-ESI calculated for $[M+H]^+$ 402, found 402.

Step 7

The hydrochloride salt of compound 10f (50.0 mg, 114 μmol) and compound 10g (43.8 mg, 343 μmol) were dissolved in 1,2-dichloromethane (4 mL), and glacial acetic acid (3.43 mg, 57.9 μmol) was added to the mixture. The reaction solution was stirred at 20° C. for 6 hours, and sodium triacetoxyborohydride (72.6 mg, 343 μmol) was added to the reaction solution. The reaction solution was stirred at 20° C. for 12 hours. The reaction solution was concentrated under reduced pressure. 10% aqueous sodium bicarbonate (10 mL) solution was added to the crude product, and the mixture was extracted with ethyl acetate (10 mL*2). The organic phases were combined, and the organic phases were washed with water (10 mL) and saturated brine (10 mL), dried with anhydrous sodium sulfate, and concentrated to obtain compound 10h.

MS-ESI calculated for $[M+H]^+$ 514, found 514.

Step 8

Compound 10h (140 mg, 273 μmol) was dissolved in anhydrous tetrahydrofuran (12 mL), and a solution of sodium hydroxide (43.6 mg, 1.09 mmol) in water (3 mL) was added to the mixture, and the reaction solution was stirred at 20° C. for 12 hours. The pH value of the reaction solution was adjusted to about 5 with 1 M hydrochloric acid solution, and the mixture was concentrated under reduced pressure, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 34%-54%, 7 minutes} to obtain compound 10.

MS-ESI calculated for $[M+H]^+$ 500, found 500.

$^1$H NMR (400 MHz, MeOH-$d_4$) δ=9.19 (d, J=2.4 Hz, 1H), 8.80 (d, J=2.4 Hz, 1H), 8.12 (d, J=7.8 Hz, 1H), 7.61 (d, J=7.3 Hz, 1H), 7.53-7.45 (m, 1H), 5.68-5.53 (m, 1H), 4.07-3.67 (m, 3H), 3.55-3.36 (m, 4H), 3.11-2.95 (m, 1H), 2.78-2.67 (m, 2H), 2.58-2.23 (m, 6H), 1.47 (d, J=6.2 Hz, 6H).

Embodiment 11

Compound 11

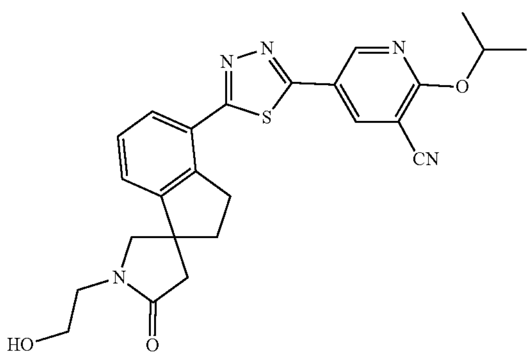

Synthetic Route:

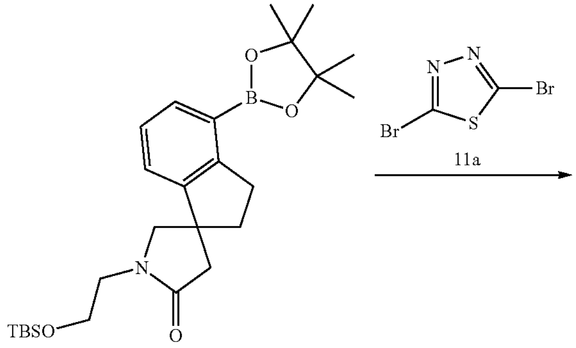

4d

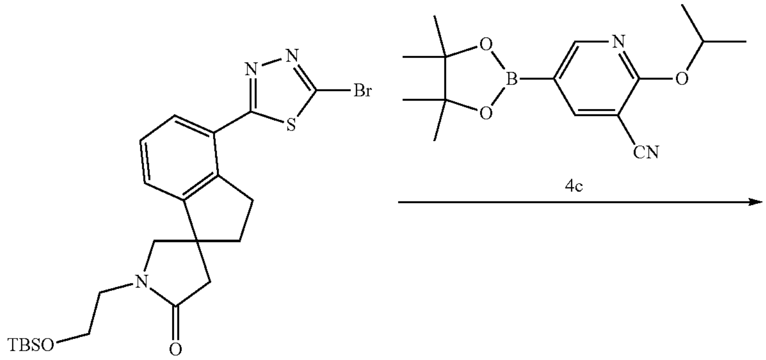

11b

-continued

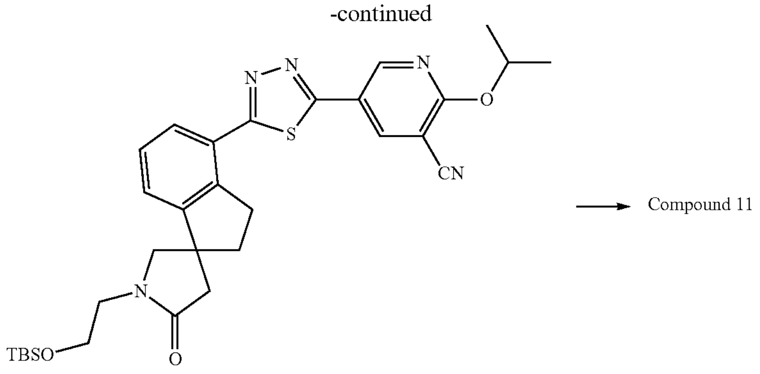

11c

Step 1

Compound 4d (200 mg, 424 μmol), compound 11a (103 mg, 424 μmol), potassium phosphate (180 mg, 848 μmol) and 1,1-bis(diphenylphosphino)ferrocene dichloropalladium (31.0 mg, 42.4 μmol) were dissolved in dioxane (3 mL) and water (1 mL). Under nitrogen protection, the reaction solution was stirred at 80° C. for 12 hours, and the reaction solution was concentrated under reduced pressure. 15 mL of water was added to the residue, and the mixture was extracted with ethyl acetate (10 mL×2). The organic phases were combined, and the organic phases were washed with saturated brine (10 mL), dried with anhydrous sodium sulfate, and the crude product was purified by thin layer chromatography (1:1, petroleum ether/ethyl acetate, Rf=0.17) to obtain compound 11b.

MS-ESI calculated for $[M+H]^+$ 508 and 510, found 508 and 510.

Step 2

Compound 11b (40.0 mg, 78.6 μmol), compound 4c (22.6 mg, 78.6 μmol), potassium phosphate (33.4 mg, 157 μmol) and 1,1-bis(diphenylphosphino)ferrocene dichloropalladium (5.76 mg, 7.87 μmol) were dissolved in dioxane (3 mL) and water (1 mL). Under nitrogen protection, the reaction solution was stirred at 80° C. for 12 hours, and the reaction solution was concentrated under reduced pressure. 15 mL of water was added to the residue, and the mixture was extracted with ethyl acetate (10 mL×2). The organic phases were combined, and the organic phases were washed with saturated brine (10 mL×2), dried with anhydrous sodium sulfate, and concentrated to obtain compound 11c.

MS-ESI calculated for $[M+H]^+$ 590, found 590.

Step 3

Compound 11c (56.0 mg, 94.9 μmol) was dissolved in ethyl acetate (1 mL), and ethyl acetate hydrochloride (4 M, 1 mL) solution was added to the mixture. The reaction solution was stirred at 20° C. for 1 hour, and the reaction solution was concentrated under reduced pressure. The crude product was purified by high performance liquid chromatography (hydrochloric acid condition, column type: Phenomenex luna C18 150*25 mm*10 μm; mobile phase: [water (0.05% HCl)-acetonitrile]; acetonitrile %: 38%-68%, 10 minutes) to obtain compound 11.

MS-ESI calculated for $[M+H]^+$ 476, found 476.

$^1$H NMR (400 MHz, $CDCl_3$) δ=8.93 (d, J=2.4 Hz, 1H), 8.52 (d, J=2.4 Hz, 1H), 7.86-7.76 (m, 1H), 7.48-7.35 (m, 2H), 5.58-5.47 (m, 1H), 3.91-3.78 (m, 2H), 3.72-3.45 (m, 4H), 3.40 (t, J=7.2 Hz, 2H), 2.79 (d, J=16.8 Hz, 1H), 2.69 (d, J=16.8 Hz, 1H), 2.43-2.24 (m, 2H), 1.46 (d, J=6.4 Hz, 6H).

Test Embodiment 1: In Vitro Evaluation of the Agonistic Activity of the Compounds of the Present Disclosure on S1PR1

Experimental Objective: To Detect the Agonistic Activity of Compounds on S1PR1

I. Cell Treatment

1. A PathHunter cell line was thawed according to standard procedures;
2. the cells were inoculated in a 20 μL 384-well microplate and incubated at 37° C. for appropriate time.

II. Agonist

1. For agonist determination, cells were incubated with samples to be tested to induce a reaction;
2. a storage solution to be tested was 5-fold diluted into a buffer;
3. 5 μL of the 5-fold dilution was added to the cells and incubated at 37° C. for 90-180 minutes. The vehicle concentration was 1%.

III. Signal Detection 1. 12.5 μL or 15 μL of PathHunter detection reagent at a volume ratio of 50% was added at a time, and then incubated at room temperature for 1 hour to generate a detection signal;
2. the microplate was read with a PerkinElmer Envision™ instrument for chemiluminescent signal detection.

IV. Data Analysis

1. Activity analysis of the compound was carried out by using CBIS data analysis kit (ChemInnovation, CA);
2. Calculation formula:

% activity=100%×(average test sample RLU−average vehicle RLU)/(average maximum control ligand−average vehicle RLU)

Experimental results are shown in Table 1:

TABLE 1

| S1PR1 agonistic activity test results | |
|---|---|
| Sample for test | S1PR1 agonistic activity, Emax |
| Compound 1 | 0.134 nM, 99.3% |
| Compound 3 | 4.46 nM, 62.8% |

TABLE 1-continued

| S1PR1 agonistic activity test results | |
|---|---|
| Sample for test | S1PR1 agonistic activity, Emax |
| Compound 4 | 20.9 nM, 67.6% |
| Compound 5 | 24.3 nM, 63.5% |
| Compound 6 | 7.1 nM, 78.5% |
| Compound 7 | 2.84 nM, 88.1% |
| Compound 8 | 1.25 nM, 110% |
| Compound 9 | 0.613 nM, 104% |
| Compound 10 | 0.474 nM, 92.0% |
| Compound 11 | 6.12 nM, 104% |

Conclusion: the compounds of the present disclosure all have significant or even unexpected S1PR1 agonistic activity.

Test Embodiment 2: Pharmacokinetic Evaluation of Compound in Rats

Experimental Objective: To Test the Pharmacokinetics of the Compound in SD Rats

Experimental Materials:

Sprague Dawley rat (male, 200-300 g, 7-9 weeks old, Shanghai SLAC)

Experimental Operation:

A standard protocol was used to test the pharmacokinetic characteristics of rodents after intravenous injection and oral administration of the compound. In the experiment, the candidate compound was prepared into a clear solution, and administrated to rats by single intravenous injection and oral administration. The vehicle for intravenous injection was a 5:95 DMSO and 10% hydroxypropyl β-cyclodextrin aqueous solution, and the vehicle for oral administration was a 0.5% w/v methylcellulose and 0.2% w/v tween 80 aqueous solution. Whole blood samples within 24 hours were collected, centrifuged at 3000 g for 15 minutes, and the supernatant was separated to obtain plasma samples. Four times the volume of acetonitrile solution containing internal standard was added thereto to precipitate protein. The mixture was centrifuged, and the supernatant was taken, and an equal volume of water was added thereto. Then the mixture was centrifuged and the supernatant was taken for injection. The blood drug concentration was quantitatively analyzed by LC-MS/MS analysis method, and pharmacokinetic parameters, such as peak concentration, clearance rate, tissue distribution, half-life, area under the drug-time curve and bioavailability, were calculated.

Experimental Results:

TABLE 2

| Pharmacokinetic test results | | | | | | | |
|---|---|---|---|---|---|---|---|
| Sample for test | Dosage of administration | Peak concentration $C_{max}$ (ng/mL) | Clearance rate CL (mL/min/kg) | Tissue distribution Vdss (L/kg) | Half-life $T_{1/2}$ (PO, h) | Area under the drug-time curve $AUC_{0\text{-}last}$ PO (nM · hr) | Bioavailability F (%) |
| Compound 1 | Intravenous injection (1.0 mg/kg) Oral administration (3.0 mg/kg) | 3100 | 1.66 | 1.18 | 7.22 | 35541 | 71.9 |

Conclusion: the compounds of the present disclosure show good bioavailability, high area under the drug-time curve and low clearance rate in the pharmacokinetics of SD rats.

Test Embodiment 3: Pharmacokinetic Evaluation of Compound in Mice

Experimental Objective: To Test the Pharmacokinetics of the Compound in CD-1 Mice Experimental Materials:

CD-1 mice (male, 20-40 g, 6-10 weeks old, Shanghai BK)

Experimental Operation:

The standard protocol was used to test the pharmacokinetic characteristics of rodents after intravenous injection and oral administration of the compound. In the experiment, the candidate compound was prepared into a clear solution, and administrated to two mice by single intravenous injection and oral administration. The vehicle for intravenous injection was a 5:95 DMSO and 10% hydroxypropyl β-cyclodextrin aqueous solution, and the vehicle for oral administration was a 0.5% w/v methylcellulose and 0.2% w/v tween 80 aqueous solution. Whole blood samples within 24 hours were collected, centrifuged at 3200 g for 10 minutes, and the supernatant was separated to obtain plasma samples. Four times the volume of acetonitrile solution containing internal standard was added thereto to precipitate protein. The mixture was centrifuged, and the supernatant was taken, and an equal volume of water was added thereto. Then the mixture was centrifuged and the supernatant was taken for injection. The blood drug concentration was quantitatively analyzed by LC-MS/MS analysis method, and pharmacokinetic parameters, such as peak concentration, tissue distribution, clearance rate, half-life, area under the drug-time curve and bioavailability, were calculated.

Experimental Results:

TABLE 3

| Pharmacokinetic test results | | | | | | | |
|---|---|---|---|---|---|---|---|
| Sample for test | Dosage of administration | Peak concentration $C_{max}$ (ng/mL) | Clearance rate CL (mL/min/kg) | Tissue distribution Vdss (L/kg) | Half-life $T_{1/2}$ (PO, h) | Area under the drug-time curve $AUC_{0\text{-}last}$ PO (nM · hr) | Bioavailability F (%) |
| Compound 1 | Intravenous injection (0.5 mg/kg) Oral administration (2.0 mg/kg) | 2830 | 3.42 | 0.902 | 3.50 | 21299 | 100 |

Conclusion: the compounds of the present disclosure show good bioavailability, high area under the drug-time curve and low clearance rate in the pharmacokinetics of CD-1 mice.

What is claimed is:

1. A compound represented by formula (I) or a pharmaceutically acceptable salt thereof, (I)

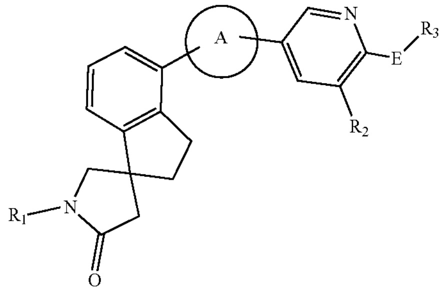

wherein,

E is O;

ring A is 1,2,4-oxadiazolyl;

$R_1$ is selected from $C_{1-3}$ alkyl and cyclobutyl, and the $C_{1-3}$ alkyl and cyclobutyl are optionally substituted by 1, 2 or 3 $R_a$, $R_2$ is CN;

$R_3$ is $C_{1-6}$ alkyl; and $R_a$ is independently selected from OH and COOH, respectively.

2. The compound or the pharmaceutically acceptable salt thereof according to claim 1, wherein, ring A is

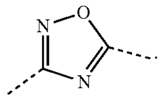

3. The compound or the pharmaceutically acceptable salt thereof according to claim 1, wherein, $R_1$ is selected from $CH_3$, $CH_2CH_3$, $CH_2CH_2CH_3$ and

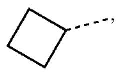

and the $CH_3$, $CH_2CH_3$ and

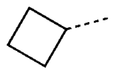

are optionally substituted by 1, 2 or 3 $R_a$.

4. The compound or the pharmaceutically acceptable salt thereof according to claim 1, wherein, $R_1$ is selected from $CH_2CH_2OH$, $CH_2COOH$, $CH_2CH_2COOH$ and

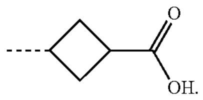

5. The compound or the pharmaceutically acceptable salt thereof according to claim 1, wherein, $R_3$ is $C_{1-3}$ alkyl.

6. The compound or the pharmaceutically acceptable salt thereof according to claim 1, wherein, the structural moiety

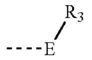

is selected from

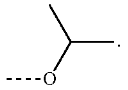

7. The compound or the pharmaceutically acceptable salt thereof according to claim 1, wherein the compound is (I-1)

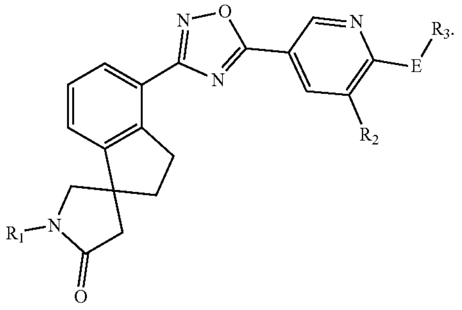

8. A compound represented by the following formula or a pharmaceutically acceptable salt thereof, selected from:

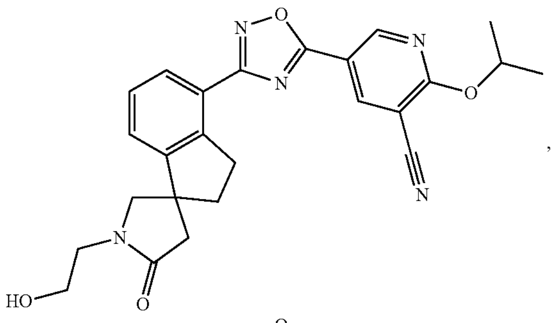

,

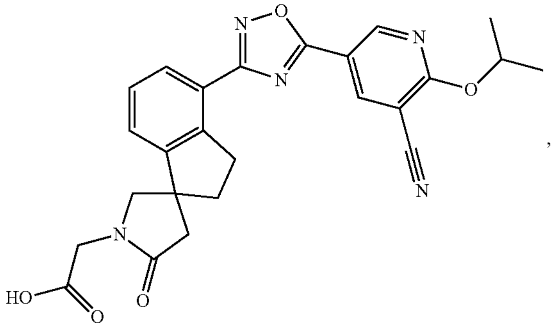

,

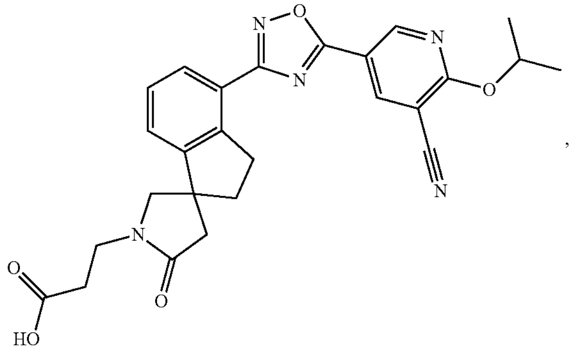

,

-continued and

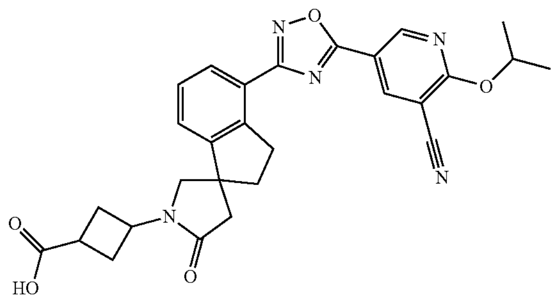

.

9. A method for activating S1PR1 in a subject in need thereof, comprising: administering an effective amount of the compound or the pharmaceutically acceptable salt thereof according claim 1 to the subject.

10. A compound represented by the following formula or a pharmaceutically acceptable salt thereof, selecting from,

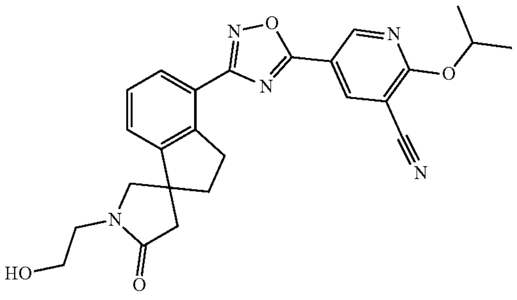

and

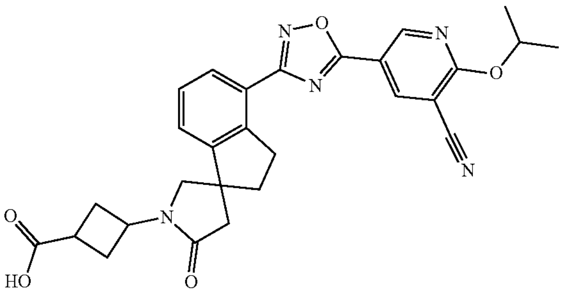

.

* * * * *